US011419587B2

(12) United States Patent
Robbins et al.

(10) Patent No.: US 11,419,587 B2
(45) Date of Patent: Aug. 23, 2022

(54) LIQUID COLLECTION DEVICE

(71) Applicant: Porex Corporation, Fairburn, GA (US)

(72) Inventors: Avi Robbins, Atlanta, GA (US); Robert Carpio, III, Suwanee, GA (US); Yuan Chang, Atlanta, GA (US); Kathleen Fitzpatrick, Blacksburg, VA (US); Rahul Maharsia, Peachtree City, GA (US); Saman Mahdavi Shahidani, Decatur, GA (US); Hayden Shelly, Atlanta, GA (US); Micah Streiff, Decatur, GA (US)

(73) Assignee: Porex Corporation, Fairburn, GA (US)

( * ) Notice: Subject to any disclaimer, the term of this patent is extended or adjusted under 35 U.S.C. 154(b) by 0 days.

(21) Appl. No.: 17/459,508

(22) Filed: Aug. 27, 2021

(65) Prior Publication Data

US 2022/0061822 A1    Mar. 3, 2022

Related U.S. Application Data

(60) Provisional application No. 63/071,870, filed on Aug. 28, 2020, provisional application No. 63/089,409, filed on Oct. 8, 2020, provisional application No. 63/132,819, filed on Dec. 31, 2020.

(51) Int. Cl.
*A61B 10/00* (2006.01)
*B01L 3/00* (2006.01)

(52) U.S. Cl.
CPC ........ *A61B 10/0051* (2013.01); *B01L 3/5023* (2013.01); *B01L 2200/0689* (2013.01);
(Continued)

(58) Field of Classification Search
CPC .............. A61B 10/0051; B01L 3/5023; B01L 2200/0689; B01L 2300/0681;
(Continued)

(56) References Cited

U.S. PATENT DOCUMENTS

| | | | |
|---|---|---|---|
| 4,596,157 A | | 6/1986 | Laauwe |
| 5,494,646 A | * | 2/1996 | Seymour ............ A61B 5/15142 |
| | | | 435/287.7 |

(Continued)

FOREIGN PATENT DOCUMENTS

| | | |
|---|---|---|
| WO | 1995/02996 A1 | 2/1995 |
| WO | 2012/163788 A1 | 12/2012 |

(Continued)

OTHER PUBLICATIONS

Invitation to Pay Additional Fees and, Where Applicable, Protest Fee, PCT Patent Application No. PCT/US2021/048010, dated Dec. 10, 2021, 8 pages.

*Primary Examiner* — Christopher L Chin
(74) *Attorney, Agent, or Firm* — Kilpatrick Townsend & Stockton LLP

(57) ABSTRACT

A liquid specimen collection device. Various embodiments implement oral fluid collection, extraction, storage, and/or testing. The device can be used to collect fluid, and to then extract and prepare the fluid for analysis, which can eliminate human error in collection and reduce complexity in diagnostic analysis. The disclosed device may be used to collect any liquid specimen. Any instance when liquid should be collected, stored, and tested may benefit from use of this disclosure.

18 Claims, 30 Drawing Sheets

(52) U.S. Cl.
CPC ............... *B01L 2300/0681* (2013.01); *B01L 2300/0825* (2013.01)

(58) Field of Classification Search
CPC ....... B01L 2300/0825; B01L 2200/028; B01L 2200/0684; B01L 2300/042; B01L 2300/048; B01L 3/52; B01L 3/532
USPC .......... 73/864; 422/527, 521, 520, 519, 422, 422/513, 534, 186.1, 616, 405, 413, 418, 422/419, 549, 411, 550, 559, 568; 427/2.3; 435/970, 286.4, 286.5, 287.7, 435/288.1, 288.2; 436/46; 600/573, 575, 600/576; 604/317, 318, 322, 324
See application file for complete search history.

(56) References Cited

U.S. PATENT DOCUMENTS

| | | | |
|---|---|---|---|
| 5,849,505 A * | 12/1998 | Guirguis | B01L 3/5635 436/514 |
| 6,489,172 B1 | 12/2002 | Bachand et al. | |
| 6,612,997 B1 | 9/2003 | Hutton | |
| 6,634,243 B1 * | 10/2003 | Wickstead | B01L 3/502 422/417 |
| 6,821,788 B2 * | 11/2004 | Cesarczyk | A61B 10/0045 436/169 |
| 7,083,754 B1 | 8/2006 | Färber | |
| 7,114,403 B2 | 10/2006 | Wu et al. | |
| 7,282,181 B2 | 10/2007 | Hudak et al. | |
| 7,618,591 B2 | 11/2009 | Slowey et al. | |
| 7,850,922 B2 | 12/2010 | Gallagher et al. | |
| 7,927,562 B2 | 4/2011 | Wan et al. | |
| 8,025,849 B2 | 9/2011 | Baldwin et al. | |
| 10,660,619 B2 | 5/2020 | Shastry et al. | |
| 2004/0237674 A1 * | 12/2004 | Wu | B01L 3/5029 73/864 |
| 2012/0067144 A1 | 3/2012 | Slowey et al. | |
| 2019/0046976 A1 * | 2/2019 | Ronsick | B01L 3/0296 |

FOREIGN PATENT DOCUMENTS

| | | | | |
|---|---|---|---|---|
| WO | 2014/190355 A1 | 11/2014 | | |
| WO | WO-2018078266 A1 * | 5/2018 | ......... | A61B 10/0045 |

* cited by examiner

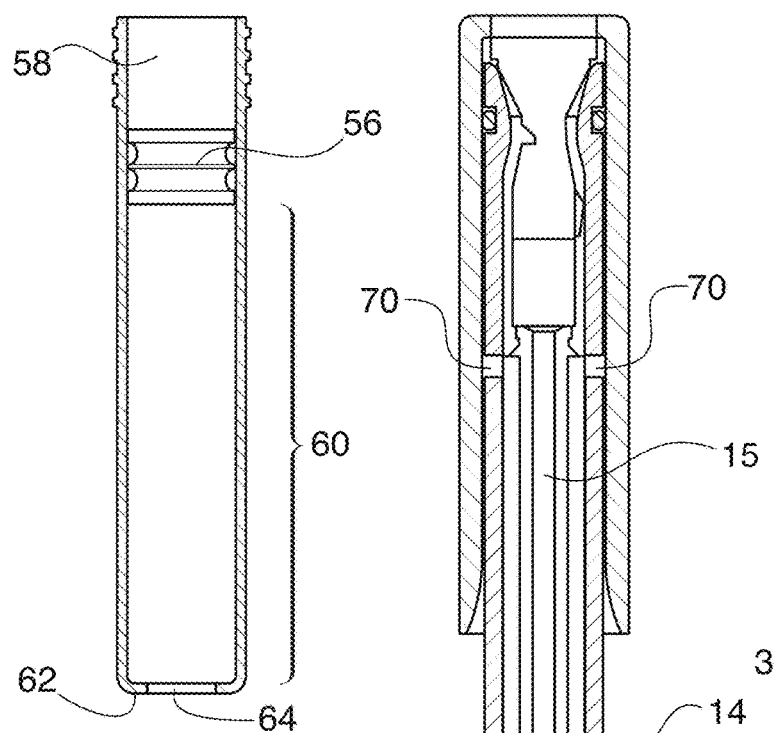
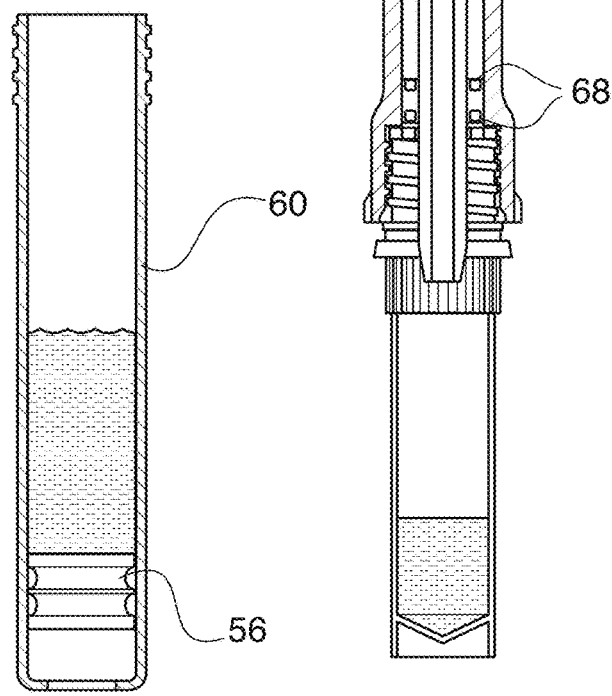
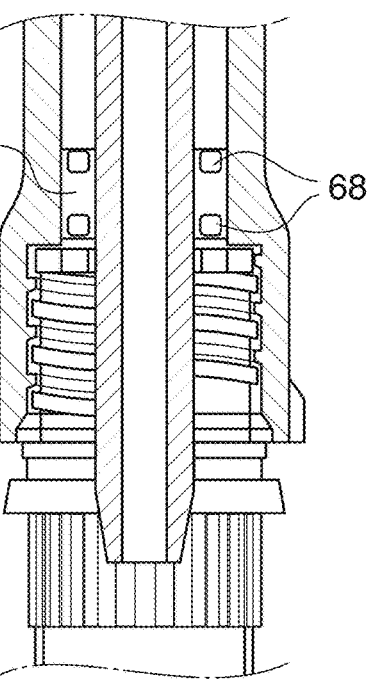
FIG. 9A
FIG. 9B  FIG. 10A  FIG. 10B

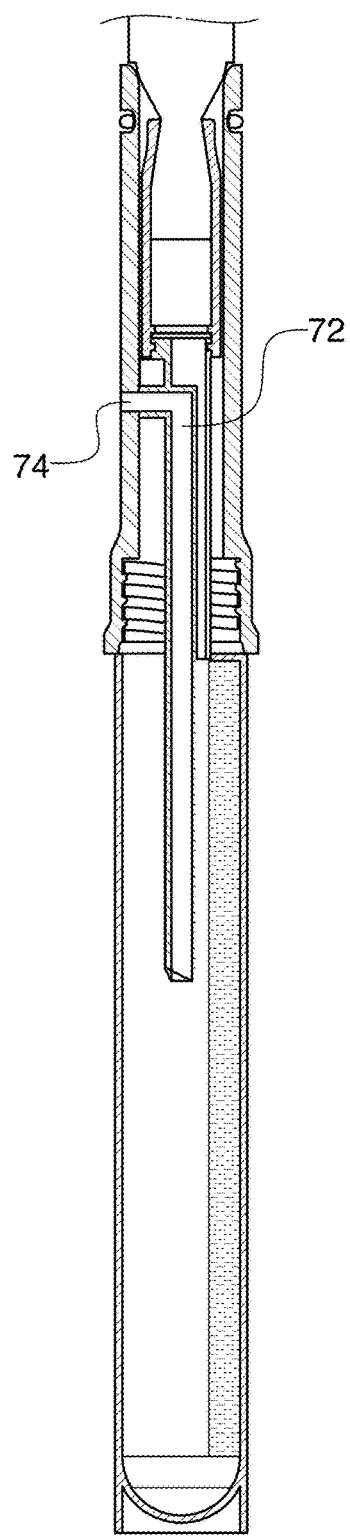
FIG. 11A
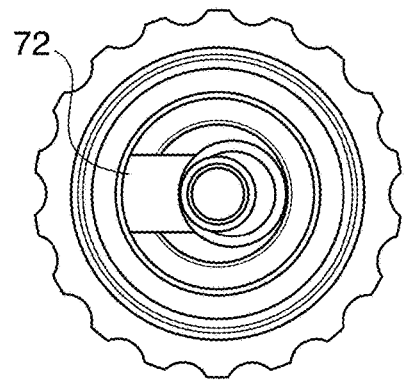
FIG. 11B
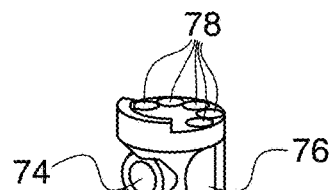
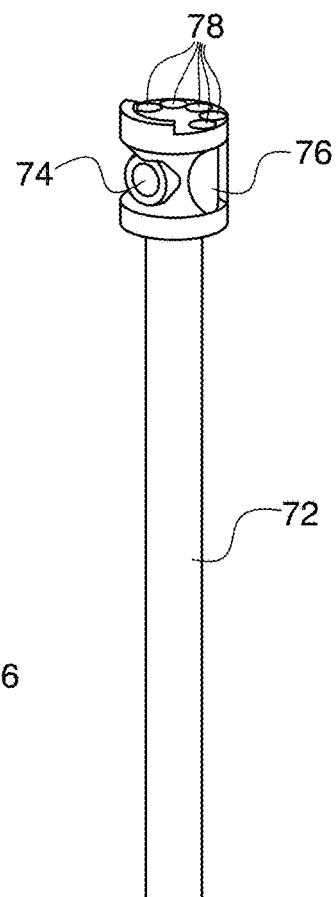
FIG. 11C
FIG. 11D

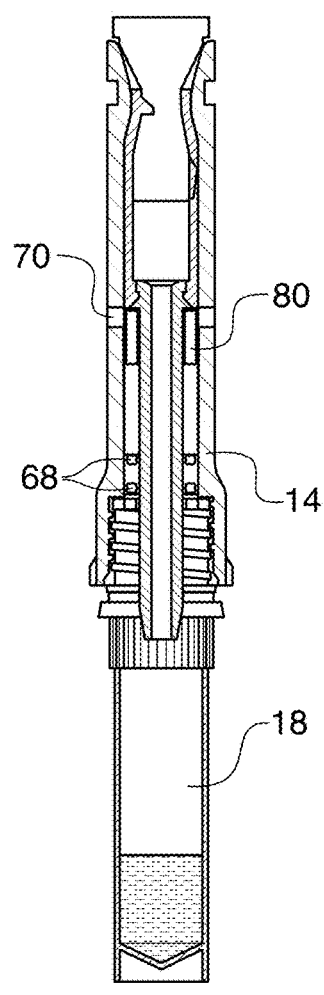
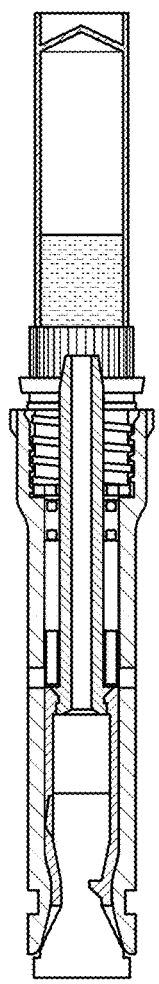
FIG. 12A  FIG. 12B
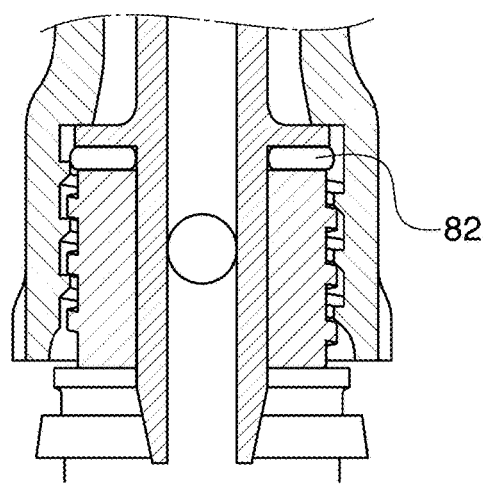
FIG. 13A
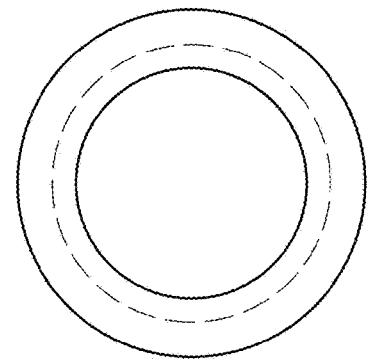
FIG. 13B
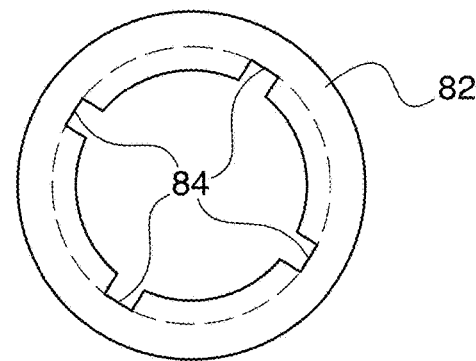
FIG. 13C

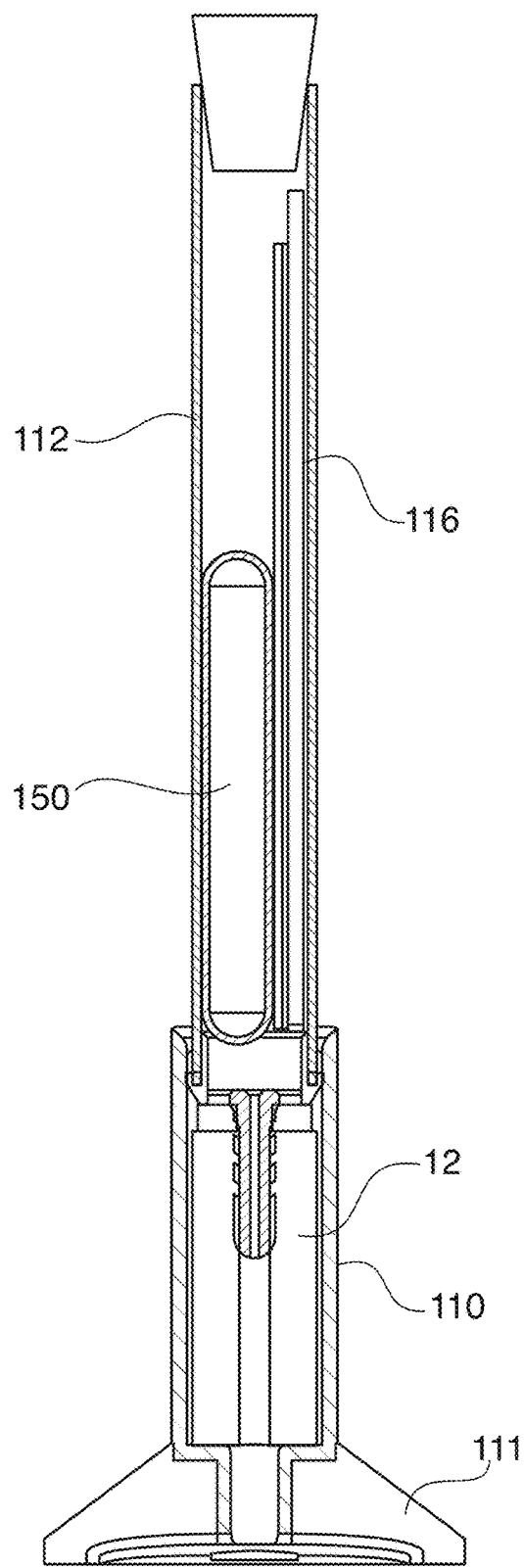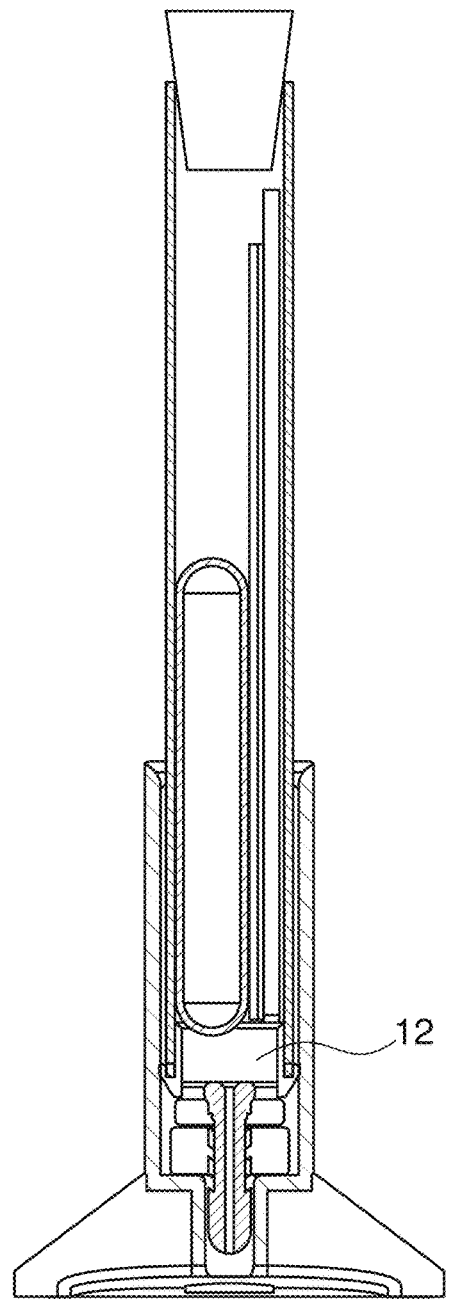
FIG. 24A
FIG. 24B

LIQUID COLLECTION DEVICE

This application claims the benefit of U.S. Provisional Application Ser. No. 63/071,870, titled "Oral Fluid Collection Extraction and Purification Device and Methods of the Same," filed Aug. 28, 2020; U.S. Provisional Application Ser. No. 63/089,409, titled "Oral Fluid Collection Device," filed Oct. 8, 2020; and U.S. Provisional Application Ser. No. 63/132,819, titled "Liquid Collection Device," filed Dec. 31, 2020, the entire contents of which are hereby incorporated by reference.

FIELD OF THE DISCLOSURE

According to certain embodiments of this disclosure, there is provided a liquid specimen collection device. Various embodiments implement oral fluid collection, extraction, storage, and/or testing. The device can be used to collect fluid, and to then extract and prepare the fluid for analysis, which can eliminate human error in collection and reduce complexity in diagnostic analysis. The disclosed device may be used to collect any liquid specimen. Any instance when liquid should be collected, stored, and tested may benefit from use of this disclosure.

BACKGROUND

Oral fluid collection devices are widely used in the medical diagnostics industry for safe and convenient sample collection and disease identification. For examples, U.S. Pat. Nos. 9,198,641; 5,339,829; and 8,025,851 disclose devices that use a plunger, a collection pad, an adequacy indicator buffer, a compression seal, a filter, and a cartridge in various forms and combinations. There are also saliva collection systems manufactured by DNA Genotek, Ancestry, Oasis Diagnostics Corp., and Saliva Diagnostic Systems.

All the above disclosures focus on sufficiency and filtration of macro level particulates. In many applications, it is desirable to filter out specific molecular particulates such as proteins including mucins, amylases, albumin, etc. from the oral fluid. It is also desirable that some components are added to or extracted from the fluid sample prior to processing in a lab. Existing methods of collecting passive drool in a cup are prone to errors which can impact the efficacy of testing. Other methods of using an absorbent pad to collect the saliva does not provide sufficient filtration options, sufficient usability, or sufficient transport options for ease and use. Accordingly, the present disclosure addresses these needs.

SUMMARY

The present disclosure relates to a fluid sample collection device that can indicate sample sufficiency, filter specific proteins and cellular debris from the sample, add reagents to the collected sample, transport the sample to testing lab, receive a test strip to test the sample on site, or any combination thereof. The disclosed device can be used in applications ranging from human genomics, infectious disease testing, hormone testing, drug testing, microbiome testing, non-infectious disease testing, or any other appropriate test that can use a body fluid as a base sample. The disclosed device is particularly suited for collection of oral fluid such as saliva, but it should be understood that it may be used in connection with collecting and testing of other fluids as well. The disclosed device may be used to collect any liquid specimen, including but not limited to oral fluid/saliva, urine, blood, sweat, tears, or any other fluid. It may also be used to collect liquid from a stream or puddle for further testing. Any instance when liquid should be collected, stored, and tested may benefit from use of this disclosure.

It is generally envisioned that the collected fluid, which is described herein as being bodily fluid such as saliva, may be collected for various types of testing.

The device can purify samples during storage and transport to remove cells, mucins, and debris such that centrifuging steps or other chemical filtration steps such as solid phase extraction may not be required prior to analysis. The device can also extract nucleic acids from the sample such that nucleic acid extraction steps may not be required in a lab prior to analysis. These various types of testing include but are not limited to diagnostic testing, testing for infectious disease or other afflictions, genetic testing, hormone testing, endocrinology testing, drug testing, microbiome testing, non-infectious disease testing (for any type of health area such as cancer testing, cardiology testing, diabetes testing, or any other appropriate testing that can be done with bodily fluids) or any type of tests that may be run on collected fluid in order to identify an internal condition of a subject. It is also possible for the testing to include chemical testing, water chemistry analysis, chlorine testing, contaminant testing, or any other appropriate analysis that may be conducted on a liquid.

In one example, there is provided a fluid collection device, comprising: a collection pad; a device body; and a collection container, wherein the collection pad is secured to a first end of the device body and wherein the collection container is positioned at a second end of the device body.

In the above or any subsequent examples, the collection container may be integrally formed with the device body to provide a one-piece device.

In any of the above or any subsequent examples, the collection container may be removeably secured to the device body. For example, the collection container may be threadingly secured to the device body.

In any of the above or any subsequent examples, there is a nozzle positioned within the device body for directing collected fluid.

In any of the above or any subsequent examples, fluid collected via the collection pad is collected at a first end of the collection pad, travels through the collection pad, and exits at a second end of the collection pad, into the collection container.

In any of the above or any subsequent examples, there is provided a filter positioned to filter collected fluid. The filter may be fiber components, track-etched-membranes, sintered particles, or any combination thereof.

In any of the above or any subsequent examples, there may be provided a cap with a length configured to be positioned over and cover the collection pad.

In any of the above or any subsequent examples, there is a buffer, additive, or reagent incorporated into the fluid collection device. The buffer, additive, or reagent may be incorporated into the collection device via any of the following or any combination thereof: a cap that is positioned over the collection pad and when pressure is applied to the collection pad via the cap, the buffer additive, or reagent is released; a filter through which collected fluid travels on its way to the collection container; in the collection container; in a buffer pouch that releases buffer during use; in a separate buffer container; or in a separate buffer sponge.

In any of the above or any subsequent examples, there may further be a funnel positioned with respect to the device body.

In any of the above or any subsequent examples, the collection container may be a dropper bottle.

In any of the above or any subsequent examples, there may be provided one or more venting features. The one or more venting features may be a porous vent gasket, threads between the device body and the collection container, an exhaust vent, a plunger, or a vent tube with side openings on the device body.

In any of the above or any subsequent examples, there may be provided a sample sufficiency indicator.

In any of the above or any subsequent examples, there may be a moveable base.

In any of the above or any subsequent examples, a seal between the device body and the collection pad may be created by an adapter.

In any of the above or any subsequent examples, there may be provided an access point on the collection container configured to allow sample extraction from a collection container that remains integral with the device body or from a collection container that is removed from the device body.

In any of the above or any subsequent examples, there may be provided an oral fluid sample collection and testing device, comprising: a buffer solution contained within or associated with a buffer container; a collection pad for use in collecting a saliva sample from a patient; and a test strip; wherein the buffer solution and the saliva sample are contacted with one another and then contacted with the test strip.

In any of the above or any subsequent examples, the buffer solution may be provided in a buffer ampule or a buffer cup.

The terms "invention," "the invention," "this invention" "the present invention," "disclosure," "the disclosure," and "the present disclosure," used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

FIGS. 9A-9B shows side plan views of a collection container with a movable base.

FIGS. 10A-10B show side cross-sectional views of one venting option.

FIG. 11A shows a side cross-sectional view of a side to venting option.

FIG. 11B shows a top plan view of the vent tube of FIG. 11A.

FIG. 11C shows a top plan view of the vent tube of FIG. 11D.

FIG. 11D shows a side perspective view of an alternate vent tube.

FIGS. 12A-12B shows side cross-sectional views of an exhaust venting option.

FIG. 13A shows a side cross-sectional view of a venting gasket.

FIG. 13B shows a top plan view of one embodiment of a venting gasket.

FIG. 13C shows a top plan view of an alternate embodiment of a venting gasket.

FIGS. 24A-24B show side cross-sectional views of a breakable buffer ampoule.

DETAILED DESCRIPTION

In one embodiment, the device incorporates a collection pad for collecting a liquid sample, a filter, and a collection container. The device may also incorporate a cap that is used to squeeze the liquid sample that is collected by the collection pad through the filter and into the collection container. Other embodiments do not use a filter, but include a collection pad and a device body that can hold the collected sample.

Figure 1:
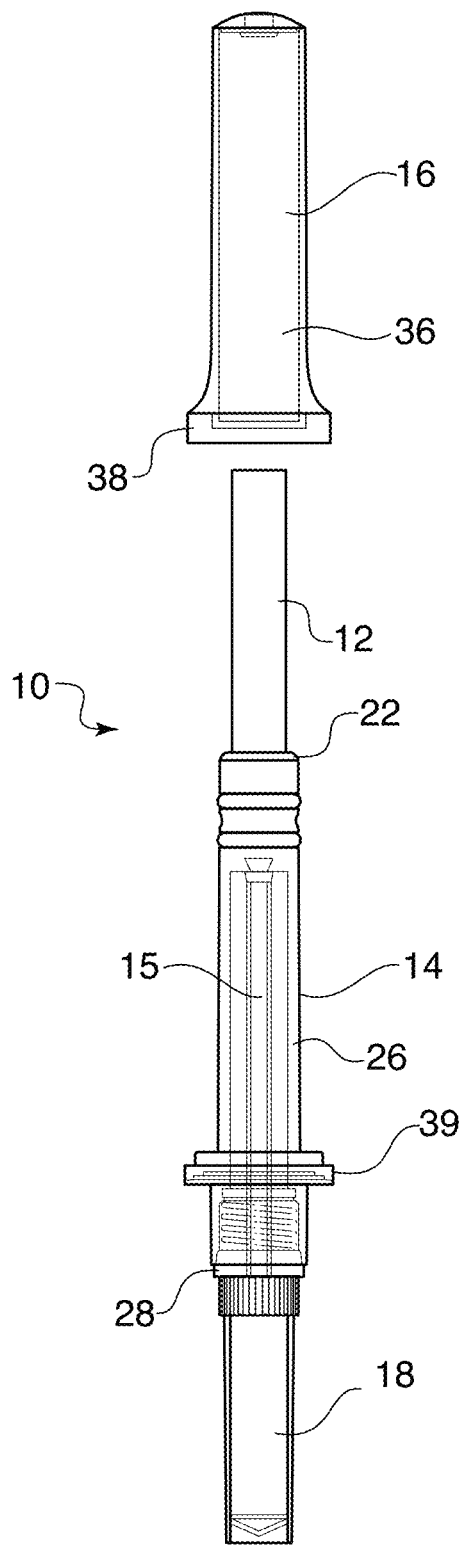
FIG. 1 shows a side plan transparent view of one embodiment of a fluid collection device.

Referring now to FIG. 1, there is shown a fluid collection device 10 that features a collection pad 12, a device body 14 that houses the collection pad, a cap 16 that provides a dual function of protection of the collection pad prior to use and compression of the fluid out of the pad, and a collection container 18. As shown by the cross section of FIG. 2, the device 10 may also be provided with a filter 20. These features are all incorporated into the single device 10, with the collection container 18 removably secured thereto. Additional features may also be incorporated into the device, as described herein. Material options for the collection pad 12 and filter 20 are described further below.

The device body 14 incorporates a collection pad 12 that is in fluid communication with the collection container 18. In a specific example, the collection pad 12 may be connected to one end of the device body 14 and the collection container 18 may be connected to the other end of the device body. Other connection options are possible, such as a direct connection or an indirect connection between the collection pad 12/device body 14 and/or the device body 14/collection container 18.

In the example illustrated by FIGS. 1-4, the device body 14 has an upper open end 22, into which the collection pad 12 may be press fit or friction fit. In alternate options, the collection pad 12 may be glued, ultrasonically welded, laser welded, heat staked, or otherwise mechanically attached using any appropriate attachment system. The collection pad 12 is sized so that it fits into the end 22 securely, but such that application of pressure can cause the collection pad 12 to be compressed and to move into the cavity 26 of the device body 14. If provided, the filter 20 is positioned below or otherwise downstream of the collection pad 12, such that compression of the collection pad 12 causes fluid contained in the collection pad 12 to be released from the pad 12 and to pass through the filter 20.

In one example, the filter 20 may have an outer diameter (OD) that closely matches the inner diameter (ID) of the upper open end 22 such that it is press fit into place. It is also possible for the OD of the upper open end 22 to have external grooves that can receive the one or more O-rings 24 for a liquid tight seal with the cap 16.

In one example, a nozzle 15 may be provided inside the device body 14, extending the length between the collection pad 12 and the collection container 18. The nozzle 15 can be a hollow tube that helps facilitate movement of the saliva to the collection container 18, after passing through the filter 20. The nozzle 15 effectively reduces the size of the cavity 26 between the collection pad 12 and the collection container 18. It is a thin hollow tube positioned within the cavity that has a smaller diameter than the diameter of the device body. The nozzle 15 allows more of the collected fluid to pass into the collection container 18 rather than getting stuck on sides of the device body during sample collection or transfer. This can be particularly useful for collection of smaller amounts of fluid, such as saliva. The nozzle 15 also extends down into the collection container 18 in order to help prevent leakage and/or splashing of the collected fluid near/around the connection between the device body 14 and the collection container 18. For example, if this connection is a threaded connection, the presence of nozzle 15 helps ensure that the collected saliva stays away from the threads when the container is opened. The nozzle 15 provides a pathway between the pad and the collection container. The nozzle can be connected to and a part of the device body 14. In the example shown by FIG. 2, the nozzle is positioned below the filter 20. In embodiments that use an internal plunger (described further below), the plunger can be designed to encircle the nozzle 15 like an elongated ring. It is possible to provide a one-way valve connected to the patient-facing end of the nozzle to ensure that saliva passes into the collection pad and into the collection container, but not to flow in the opposite direction.

Figure 6:
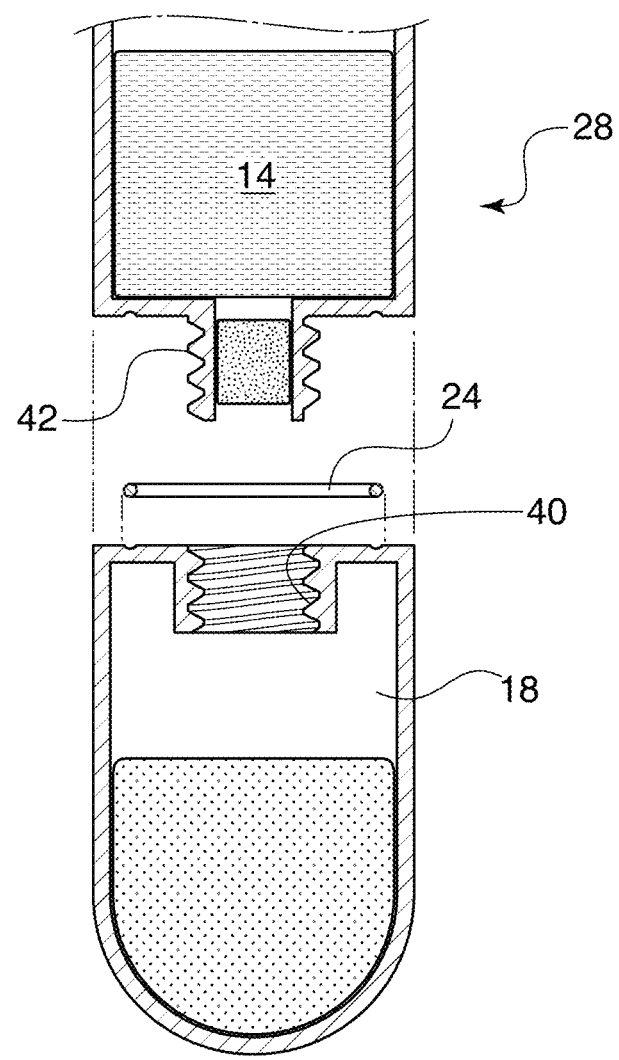
FIG. 6 shows an alternate connection option between device body and collection container.

The collection container 18 is secured at a second end 28 of the device body 14. The collection container 18 may be secured to the device body 14 in any appropriate manner. A threaded fit has been found to be most effective. Threaded connections are illustrated by FIGS. 1-5. In these examples, the collection container 18 has upper threading that is received by internal threading of the device body 14. FIG. 6 illustrates an alternate threaded connection option. In this example, the second end 28 of the device body 14 has a lower threaded end 42. The collection container has corresponding threaded receiving portion 40. It should be understood that threads 42 and the threaded receiving portion 40 may have their locations switched. It should also be understood than any other securement method may be used, such as press fit, clipping arms, magnetic attachment, or any other appropriate securement features. It should further be understood that the collection container 18 can be designed as an integral part of the device. For example, the collection container may be permanently connected to the device body. In this instance, the entire device 10 can be sent to a lab for analysis/testing of the sample, without the user having to remove the collection container. In any of the disclosed embodiments, the device (or the collection container on its own, if removable) may be inserted into an automation device as outlined below. If the collection container is not designed to be removable, it may be provided with a sample access point, such as an extraction port 206, somewhere along the device. In a specific example, the extraction port may be positioned at the lower portion or bottom of the device, as described further herein.

Figure 2:
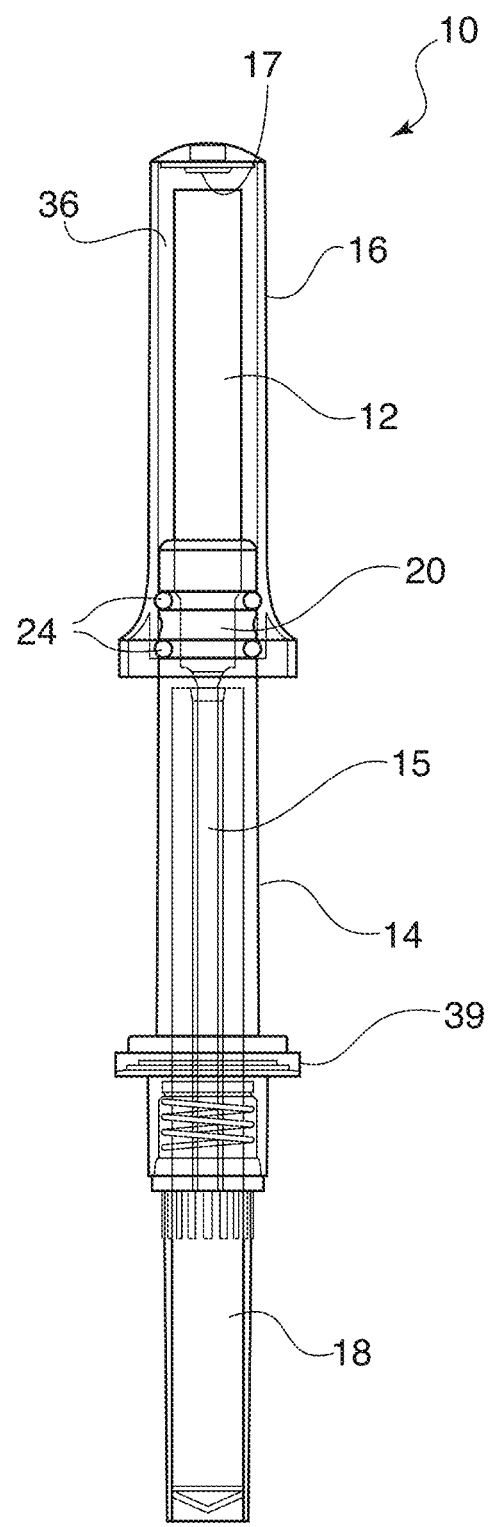
FIG. 2 shows a side plan transparent view of the fluid collection device of FIG. 1.

A cap 16 is provided to cover and protect the collection pad 12 prior to use of the device 10. In use, the cap 16 is removed and fluid is collected. Once the fluid has been collected, the cap 16 is replaced over the collection pad 12, as shown in FIG. 2, and depressed. The cap 16 is shaped with a hollow channel 36 that fits over and receives the collection pad 12. As shown, the cap 16 may have a lower flange 38 that provides a ledge-like feature for a user's thumb or fingers to achieve leverage in order to depress the cap 16 in use. There may also be provided a compression feature 17 on the inside of the cap 16 at the top. Compression feature 17 allows further/maximum compression of the collection pad 12 inside the cap cavity 36 and device body 14.

Figure 3:
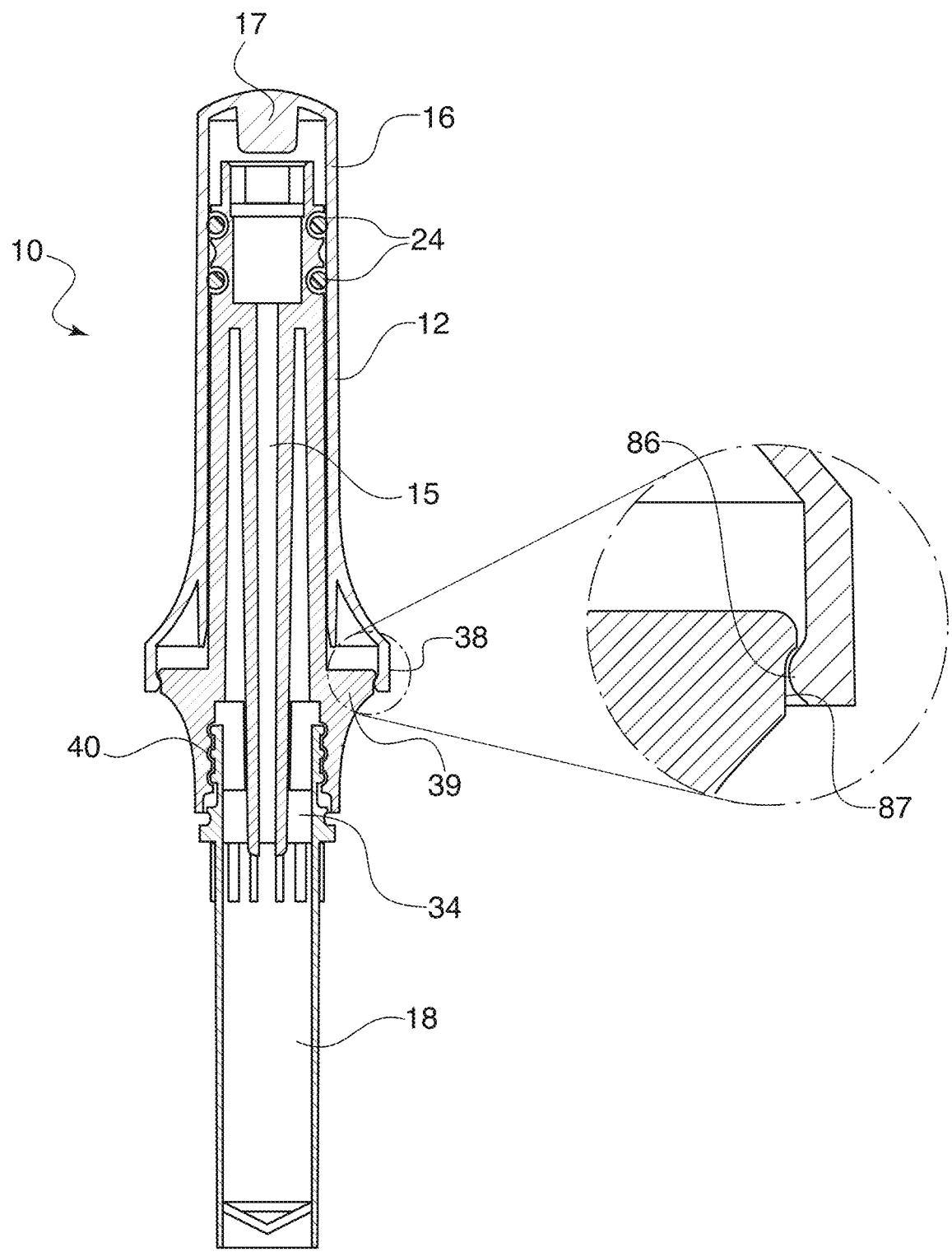
FIG. 3 shows a side cross-sectional view of the fluid collection device of FIG. 1, with the cap pushed down.
Figure 4:
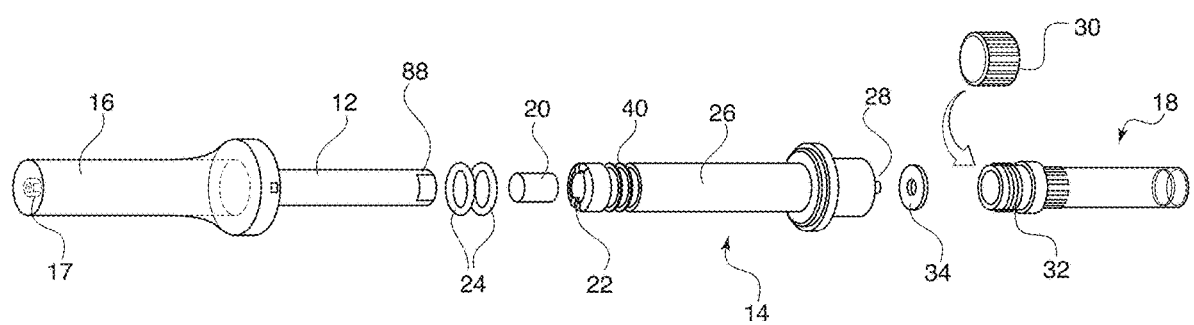
FIG. 4 shows an exploded view of the fluid collection device of FIG. 1.
Figure 5A:
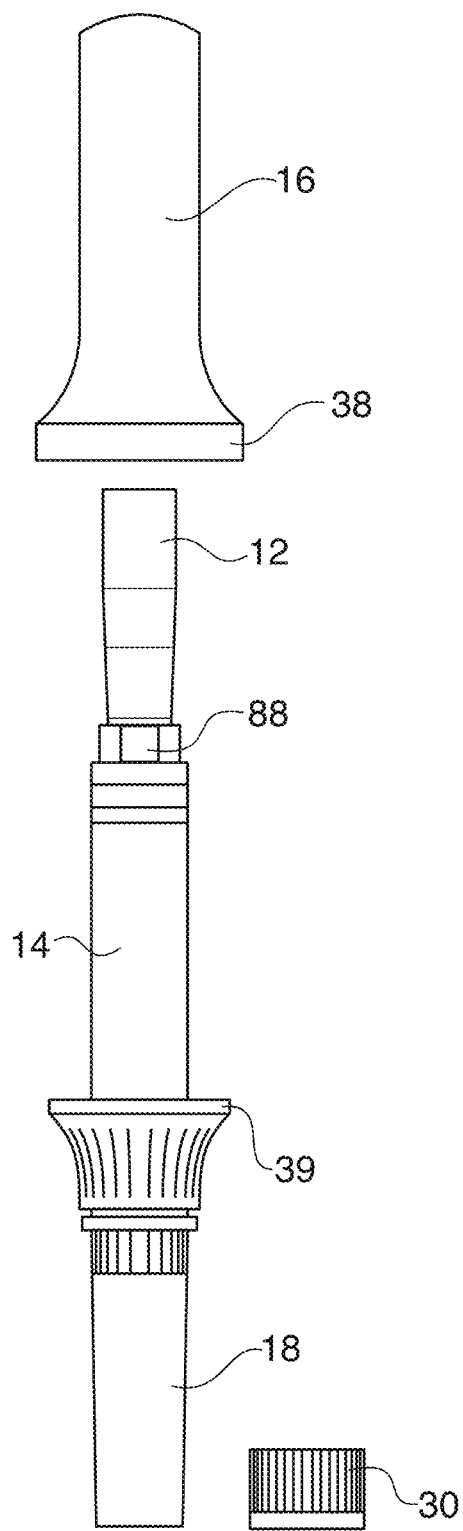
FIG. 5A shows side plan view of an alternate design of a fluid collection device.
Figure 5B:
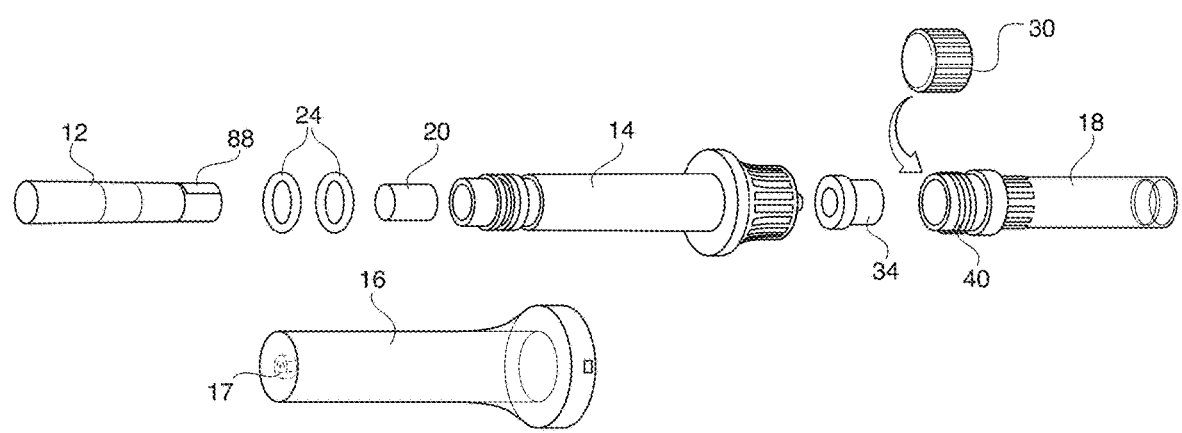
FIG. 5B shows an exploded view of the fluid collection device of FIG. 5A.

When the collection pad 12 is compressed via the cap 16, fluid contained therein is released from the collection pad 12, passes through the optional filter 20 if provided, and into the collection container 18. Because compression of the collection pad 12 takes place in the closed environment of the device 10, it may be necessary to provide a venting option in order to achieve a good compression. Various venting options are described in more detail below. FIGS. 3 and 4 illustrate one embodiment of a vent gasket 34, although any of the venting options described herein are possible and considered within the scope of this disclosure.

Figure 7A:
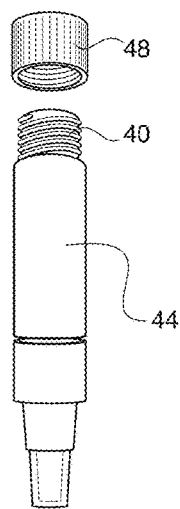
FIGS. 7A-7C illustrate alternate options for the collection container.
Figure 7B:
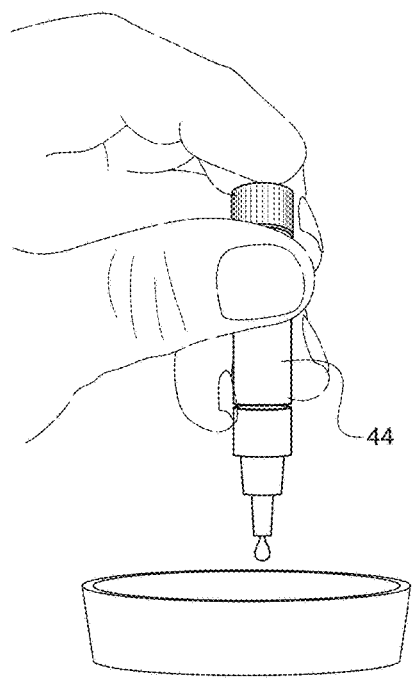
Figure 7C:
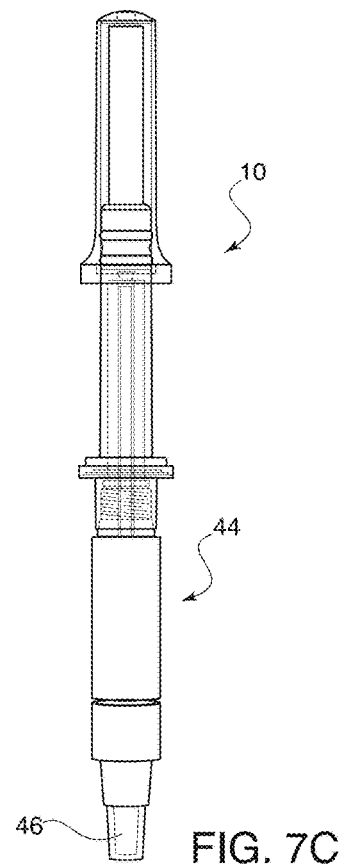
Figures 8A, 8B, 8C, 8D:
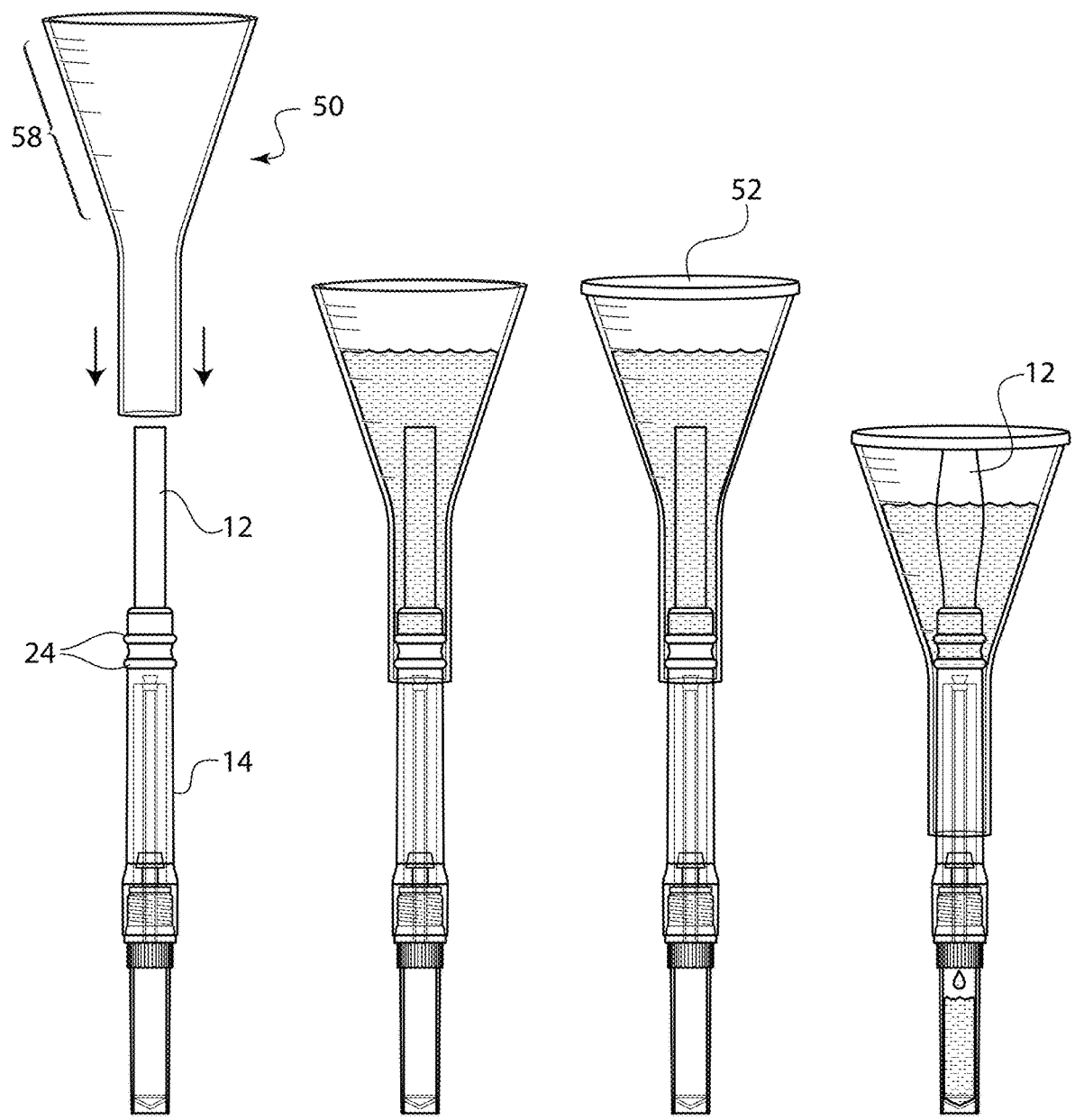
FIGS. 8A-8D show side plan views of a fluid collection device with a funnel in use.

After collection of the fluid from the collection pad 12 takes place and is delivered to collection container 18, the collection container 18 is preferably removable from the device body 14, such that the fluid can be transported elsewhere for subsequent testing/processing. A collection container cap 30 may be provided that can be secured to an upper open end 32 of the collection container 18 once it has been removed. The collection container cap 30 may be threadably secured to the upper open end 32, it may be a fliptop cap, or any other appropriate capping or sealing option. In alternate embodiments, the collection container 18 may be a squeeze tube 44, similar to an eye dropper, that is squeezed to transfer liquid to a testing assay, such as a rapid diagnostic test. Examples are shown by FIGS. 7A-7C and are described in more detail below. The dropper 44 may be removed from the device body and capped with a cap 48. Alternatively, the dropper 44 may stay attached to the device 10 and used directly.

Reference will now be made to specific features/options of the disclosed collection device 10.

Collection Pad

The fluid that may be absorbed by collection pad 12 may be any appropriate fluid to be collected and/or tested. Non-limiting examples include but are not limited to oral fluid, saliva, urine, blood, diarrhea/feces, sweat, vaginal fluids, semen, or any other appropriate fluid. Although described in connection with healthcare, it should be understood that the disclosed device may be used for a myriad of other fluid collection uses. The collection pad may be associated with a sufficiency indicator that can change color or otherwise provide a visual indication that the collection pad is sufficiently wet with the fluid to be collected.

The collection pad is intended to absorb and hold liquid, but to also release the held liquid upon compression. The material of collection pad could comprise of fibers, foams or particulate materials made from polyesters, polyurethanes, polyethylene, polypropylene, PTFE, PVDF, elastomeric materials, thermoplastic polyurethane, thermoplastic polyethylene, nylon, cellulose, cellulose acetate, natural fibers, fabric, paper, polymer hydrogel (dry form and/or wet form) such as HEMA, NIPAM, etc., a natural or man-made material, sponge, cotton, or any combination thereof. The collection pad may be treated with dried buffer, saliva-production stimulants such as citrates, materials that prevent target analyte binding to the material, surfactants to help collect and release liquid, or any other appropriate material, or any combination thereof. It is also possible to provide a hollow collection pad, such that the collection pad is a tube that has a hollow tubular length.

Cap

A cap 16 may be provided that can protect the collection pad 12 during transport and that can be pressed against the collection pad in order to force collected liquid sample out of the pad 12 and into the collection container 18. In some instances, the collected liquid sample travels through a filter on its way into the collection container 18. In a specific example, the cap 16 is designed and positioned such that it covers the collection pad 12. Pressure or force against the cap 16 can consequently apply pressure or force against the collection pad 12. This can squeeze the collected liquid through the filter (if provided) and into the collection container 18. In another specific example, the cap can form a seal with the outside of the collection device to ensure all fluid is directed through the collection pad (and optional filter) and into the collection container, and prevent leaking of fluid to the outside of the device. For example, when the cap 16 is pressed, a seal between the O-rings 24 of the side of the device body 14 and the inner diameter of the cap 16 can create a liquid-tight seal.

In use, the cap 16 is pressed onto the device body 14 and pressure causes the liquid collected in the collection pad 12 to be transferred through the device body 14, through the nozzle 15 (if provided), through an optional filter 20, and into the collection container 18. O-rings 24 positioned around an upper portion of the device body 14 can help create a liquid tight seal when the cap 16 is pressed down. Pressure from compressed air that is pressed through the device body can be released through a vent option, various options of which are described below. In one example, the vent option may be threads between the device body 14 and the collection container 18. Additional solutions are described further below. There may also be a feature 17 on the inside of the cap that adds extra compression to extract the maximum amount of liquid from the collection pad. This may be an interior plunger, spikes inside the cap, or any other appropriate feature. When the cap 16 reaches the end of its completed travel, detent features can fit over the device body 14 and engage to ensure a completed lock and snap into place. Detent features may be positioned at the end/bottom of the cap flange 38 and can snap over the body flange 39 just above where the collection container 18 is secured to the device 10.

The cap 16 and lower flange 38 may also be provided with feedback features that allow a user to know that the cap has been secured to the device body 14. Feedback features also indicate that the cap 16 has reached its full travel distance and that the swab has been fully compressed, signaling that no further action is needed and that all collected fluid available to transfer has been transferred to the collection container. In one example, the feedback features are provided as a detent/protrusion system that gives a tactile click feeling. This may be provided by a small internal protrusion 86 on the cap 16 and a similarly-shaped detent 87 on the ledge 38, which is illustrated by FIG. 3. It should also be understood that these components may be switched, such that the detent is on the cap and the protrusion is on the ledge/device body.

Filter

The filter 20 is generally positioned below (or downstream of) the collection pad 12 and functions to filter out unwanted media from the liquid collected. The filter 20 can filter out undesired particles or other contaminants in the collected sample. Providing a filter 20 can help eliminate later centrifuging steps that would otherwise be required during testing of the collected sample. Providing a filter 20 can help concentrate the sample. Providing a filter 20 can help provide sample homogenization. Bio junks such as mucin clusters can be eliminated or grinded by passing through the filter 20, thus reducing the sample viscosity and facilitating liquid handling.

Non-limiting examples of particles that may be filtered out of the sample include but are not limited to molecular particulates, cells, proteins, cellular debris, nucleic acids, mucins, glycoproteins, bacteria, viruses, large biomolecule clusters, large size bacterial particles, dust particles, fibers, other environment contaminates, or any combination thereof.

Non-limiting examples of materials that may comprise the filter include but are not limited to fiber components, track-etched-membranes, and sintered particles that can offer various porosities or void volume to the filter. Porex, the current assignee of this application, manufactures and holds patent protection on various filters and/or filtration systems that may be usable in connection with this disclosure. The filter may be used to mechanically and/or chemically filter out any of the above-described particles from the liquid sample. It is possible to incorporate reagents, additive, or buffers into the filter that can be mixed with the collected fluid as it passes through. Such reagents, additives, or buffers can be added in order stabilize the liquid sample/saliva or analytes and/or to allow more accurate detection and/or to provide for viral inactivation, viral lysis, to stop or prevent bacterial growth, or any other appropriate reason for use of reagents, additives, and/or buffers.

Collection Container

There is a tight seal made when the collection container 18 is screwed (or otherwise joined) onto the device body 14. The collection container 18 may be any type of container that can collect, hold, and/or transport a liquid sample. Embodiments include but are not limited to vials, centrifuge tubes, cryo vials, blood collection tubes, saliva collection tubes, syringes, dropper bottles with a lower dispenser tip or dropper that allows the sample to be squeezed out of the collection container once collected (and filtered, etc.), syringes, or any combination thereof.

The collection container 18 may be connected to the device body 14 in any appropriate manner. Non-limiting examples of various joining mechanisms include but are not limited to a threaded connection, a press fit connection, a cone-in-cone friction fit connection, a magnetic connection, side clip arms or fastener connection, or any other appropriate type of joining mechanism. (As described elsewhere herein, it should also be understood that the collection container may be made integral with the device body, such that the entire device is sent out for testing.) FIGS. 1-5 illustrate a collection container 18 that has upper threading 40. Upper threading 40 may cooperate with lower threading 42 of the device body 14. FIG. 6 illustrates an alternate threaded connection option. As discussed herein, this threaded connection may be designed to offer a venting option as well. Additionally or alternatively, one or more alternate vent features may be provided at the device body 14/collection container 18 connection, and are described further below.

In one embodiment illustrated by FIGS. 7A-7C, the collection container can be a vial that is a dropper bottle 44. The liquid can be collected and processed/treated in any appropriate way within the liquid collection device 10 (e.g., filtered, contacted with a reagent, etc.). Once complete, the collected liquid sample can be squeezed out of the container via a dropper end 46. In a specific example, the dropper bottle 44 has upper threading 40 that can cooperate with the lower threading 42 of the device body 14 for attachment. Once liquid has been collected, the dropper bottle 44 may be removed via unthreading and covered with a dropper bottle cap 48 for transport, as illustrated by FIG. 7A. The cap can be removed (with the vial/collection container remaining intact with the rest of the device) and the sample can be squeezed out of the device. For example, the sample can be squeezed out onto a rapid diagnostic cartridge. Liquid may be released from the dropper bottle end 46 via simple squeezing of the bottle body, as illustrated by FIG. 7B. In an alternate embodiment, the collection device 10 may remain in place over the dropper bottle 44, as shown by FIG. 7C. It is possible to incorporate reagents, additive, or buffers into the collection container that can be mixed with the collected fluid.

Regardless of configuration, the collection container 18 may be pre-filled with reagents, additives, and/or buffers. These materials be provided in liquid or dry or lyophilized (freeze-dried) form. In a further embodiment, a buffer or other reagent or additional additive may be provided associated with the collection pad 12, anywhere within the liquid collection device 10, or provided in a separate pad or container designed to release the buffer or other reagent or additional additive. This material may be any fluid, buffer, preservative, viral inactivation liquid, or any other appropriate material that can be contacted with a collected sample and help with stabilization, preservation, safe transport, lab safety, clinical safety, or support or enhance further processing for diagnosis or testing. Examples are described further below.

Funnel

In order to collect an oral fluid sample, it may be possible for the user to put the collection pad 12 directly into his/her mouth. Alternatively, there may be provided a funnel 50 at a top portion of the device body 14 that allows a user to spit into the top of the device. It is also possible for the patient to be administered an oral rinse prior to delivering saliva, which can help generate saliva. Alternatively, it is possible for a different type of fluid to be poured into the funnel 50. As shown by FIGS. 8A-8D, the funnel 50 may be positioned with respect to the device body 14 in any appropriate manner. One or more O-rings 24 may help complete the seal. The collection pad 12 may be positioned in the device body 14 as previously described as well.

The collection pad 12 can absorb some of the fluid, but the remaining fluid remains in the funnel 50. The user can then position a top/cap 52 over or within the funnel 50 and press down to compress the collection pad 12 and/or to force the fluid through the collection pad 12 (and optional filter 20, if provided) into the collection container 18. It is possible to provide a visual indicator mark 58 on the side of the funnel 50 that can show how much fluid is needed (shown as a dotted line on the funnel, indicating the level of collected fluid requested, although other indicator options are possible.) This funnel 50 embodiment can potentially eliminate a step or other component in the collection process with oral rinse or greater amounts of fluid specimens to be collected. The funnel 50 can be designed to only transfer a specific amount of liquid into the device body 14 when it is compressed and hold the rest in the funnel.

In order to collect a different type of liquid sample, the collection pad 12 may be positioned in or near the liquid to be tested. For example, if river water is being tested, the collection pad 12 can be dipped in the water. If blood is being tested, the collection pad 12 can be dipped in the blood. If urine is being tested, the user may urinate on the collection pad 12 or in the funnel 50 embodiment, if provided.

Movable Bottom

One example for venting is to provide a movable bottom or base 56 of either the collection container 18 or the device body 14 itself, collectively referred to below as a tubular body 60. In this embodiment, the tubular body 60 may have an upper opening 58 that receives the collected sample, and a moveable base 56 positioned within the tubular body 60. A lower opening 62 of the tubular body 60 is generally open, but may have an inward ledge 64 that functions as a moveable bottom stop. In one example, the movable base may be shaped like a syringe plunger end, but without a plunger shaft. An example is shown by FIGS. 9A and 9B.

In use, the movable base 56 begins positioned close to the upper opening 58 of the tubular body 60. The movable base 56 starts at the top/upper opening 58 and moves down the tubular body 60 as the tubular body 60 is filled with sample. More specifically, as the collection pad 12 is compressed (which may be via a cap or plunger or any other compression member), the movable base 56 is caused to move lower into and through the tubular body 60 as the volume of the liquid sample is moved downward (along with air that cannot be compressed, thus the function of the movable base 56 as a venting feature). The moveable base 56 may maintain a seal with the side of the tubular body 60 in order to prevent air, gas, and/or liquid from moving between the top opening 58 and the lower opening 62. This venting feature maintains the collection device as a closed system.

Venting Features

Because the liquid collection device 10 is generally a closed system, during movement of liquid sample from the collection pad 12 into the collection container 18, pressure may build up. Thus, various venting options may be provided. Any of the venting features described herein may be used individually or collectively in any of the described embodiments.

One example of a venting feature described briefly above is to provide a tortuous path through threads (or any other joining mechanism) that connect the collection pad 12 with the collection container 18 (albeit this connection is an indirect connection in most cases). These threads may be located at the bottom of the device body 14 where the collection container 18 is connected to the device body 14.

Another venting option is to provide an internal air plunger 68, as illustrated by FIGS. 10A and 10B. The movable plunger 68 can travel up the device body 14 and create a seal around the inner diameter of the device and outside the nozzle 15. In this embodiment, a plunger 68 is positioned within an internal space of the device body 14. The plunger 68 moves up when the collection container 18 is pressurized. This allows the liquid in the collection container 18 to displace the air upward. Air is then allowed to exit the device body 14 through one or more holes 70 in the device body 14. One or more of these holes may be provided in a venting gasket, described further below. In this option, at least one of the holes is in a gasket that provides an airtight seal, forcing the air up into the device body to move the plunger 68 as opposed to moving through the threads.

A further venting option illustrated by FIGS. 11A-11B is to include a side air vent tube 72. In this embodiment, upon compression of the collection pad 12, air that is forced into the collection container 18 can move up through the vent tube 72 and escape the device 10 through the side air vent hole 74. In this embodiment, the vent tube 72 has a length that reaches into the collection container. It is designed so that when the collection container is tilted, the liquid level is below the opening 74 so that only air is forced through the vent hole 74 and not any of the collected fluid.

A further embodiment of a side air vent tube 72 is illustrated by FIGS. 11C-11D. In these figures, the vent tube 72 is illustrated as having a plurality of air vent holes, at least one of which is provided as a side air vent hole 74. The tube 72 also has a vent head 76 with the at least one side air vent hole 74, as well as at least one upper air vent hole 78. In the embodiment shown, there are five upper air vent holes 78 illustrated, although it should be understood that more or fewer upper air vent hole 78 are possible and considered within the scope of this disclosure. This embodiment functions similarly to the side air vent tube 72 of FIGS. 11A-11B, but it also releases air from the top of the tube 72.

A further venting option incorporates an exhaust filter 80. This is illustrated by FIGS. 12A and 12B. FIG. 12A is the device upright, FIG. 12B is the same device tilted upside down. This embodiment may also incorporate one or more air vent holes 70 in the device body 14. In this embodiment, air is forced up into the device body 14. This may be accomplished with a plunger 68 that moves up the device body 14. This may be accomplished with an airtight connection between the threads and the collection container so the air is naturally forced up into the device body (around the nozzle 15). In these cases, it is possible for liquid to travel up as well (mostly splashing) and so this exhaust filter 80 would allow air to pass through but prevent the liquid from escaping through the vent holes 70.

Another option is to provide a venting gasket/washer 82. FIGS. 13A-13C an embodiment that does not incorporate a plunger 68, but include a gasket 82 that allows only air to pass through and not liquid. This embodiment may also incorporate an exhaust filter 80 that can catch any liquid that may unintentionally/accidentally pass through the gasket 82. Exemplary options are illustrated by FIG. 13. This embodiment provides a porous gasket 82 that can be positioned near or otherwise around threading 40, 42 between the device body 14 and the collection container 18. FIG. 13A illustrates the porous gasket 82 positioned immediately above the threading of the collection container 18. This is the point of exit that can let air escape, but does not allow liquid to pass, in order to provide a liquid tight seal with an air-vent function. The vent gasket 82 allows air to pass through while preventing liquid from passing through. This allows for the device to be held in a vertical or horizontal orientation and for the cap to be pressed multiple times without any liquid being released.

The structure of the vent gasket 82 may be a circular design with an internal opening that allows liquid to pass through the interior of the device body 14. One example is illustrated by FIG. 13B. This embodiment is a ring with an inner diameter and an outer diameter that makes a seal with the inside diameter of the device body and the outside diameter of the nozzle 15, trapped between the device body 14 and the collection container 18. This allows air to pass through the gasket from 82 the collection container 18 and into the device body 14 and/or through the threads to vent the system.

The vent gasket 82 may be made of sintered particles, fiber, foam, or track-etched-membrane. The sintered particles may be mixed with other particles, such as self-sealing particles. The sintered particles (or material combination) may be mixed with material that allows air to pass through but not liquid. One example of such a material is an IP68 rated material. Exemplary filter material that may be used for vent gasket 82 are manufactured and sold by the current assignee, Porex.

FIG. 13C illustrates a similar vent gasket option, but with a plurality of internal cutouts 84. The cutouts 84 in this embodiment are used in instances in which the gasket is not porous. (Although such cutouts may also be used on a porous gasket, if desired.) The concept behind the cutouts 84 is to have a small area only that allows air to pass through more easily but not so large that they allow liquid to pass through. In theory, if the device can be vented fast enough, it will not build up enough pressure to force the liquid out through the cutouts and/or the threads.

Sample Sufficiency Indicator

A sample sufficiency indicator may be provided. An exemplary sample sufficiency indicator 88 is illustrated by FIGS. 4, 5A, 5B, and 27A. The general goal is to provide an indicator that alerts the user (whether that is the patient, caregiver, scientist, or other user of the device) that a sufficient amount of sample has been collected in the collection pad. The sample sufficiency indicator may change color. The sample sufficiency indicator may be auditory such that is creates a sound when sufficient sample is collection. Additionally to any of these options or alternatively, the sample sufficient indicator may light up, flash, create heat or another chemical reaction, allow an image to appear, be thermochromic plastic, be expanding foam, or any combination thereof. Another embodiment/configuration of a sample sufficiency indicator 88 has an additional laminate of transparent film over the sample sufficiency indicator in order to control the timing of absorption (i.e., to control the wicking direction/speed of the indicator).

Plunger Embodiment

Figure 15A:
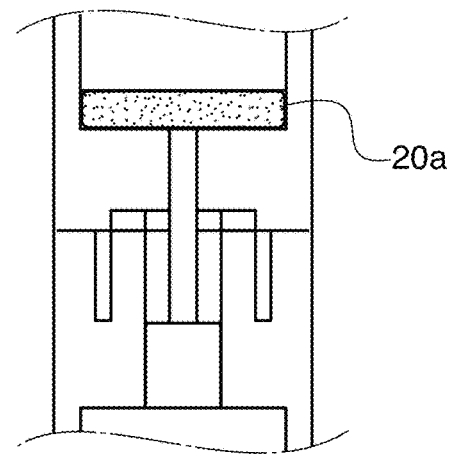
FIGS. 15A-15B show close-up views of optional filters for use.
Figure 15B:
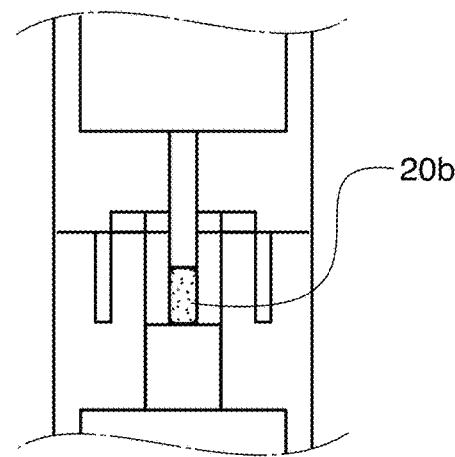
Figure 16:
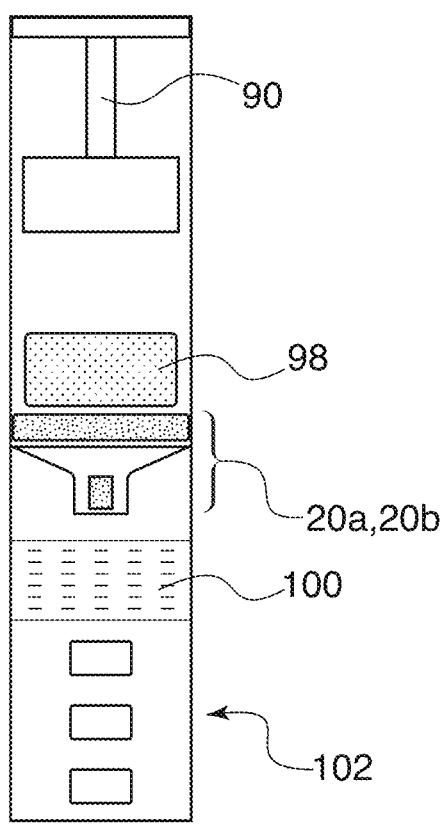
FIG. 16 shows a side schematic view of a fluid collection container that incorporates a mixing chamber.

Referring now to FIGS. 14-16, rather than using the above-described cap 16, it is possible for a push plunger 90 (such as the type used on a vial syringe) to be used in order to force liquid out of the collection pad 12 and into the collection container 18. The collection pad may have any or all of the features described herein. The plunger rod 92 may be made of polyethylene, polycarbonate, polypropylene, polyester, nylon, any other appropriate material, or any combination thereof. In one example, the plunger rod 92 may have an internal channel 94 that can receive the collection pad 12. The collection pad 12 may be positioned within the internal channel via friction fit. Once sufficient sample is collected, the collection pad/plunger assembly is inserted into a syringe body 96. Syringe body 96 generally has features of the above described device body 14. The syringe body 96 may be made from polypropylene, polyethylene, and polycarbonate. A sealing mechanism may be provided that prevents any liquid leakage or aerosolization. This is typically an O-ring 24 at the interface between plunger 90 and the syringe body 96. Once the plunger 90 is inserted, pressure can be applied to the bottom portion of the plunger in order to release oral fluid into the collection container 18 (which may have any of the above described features).

Figures 14A, 14B:
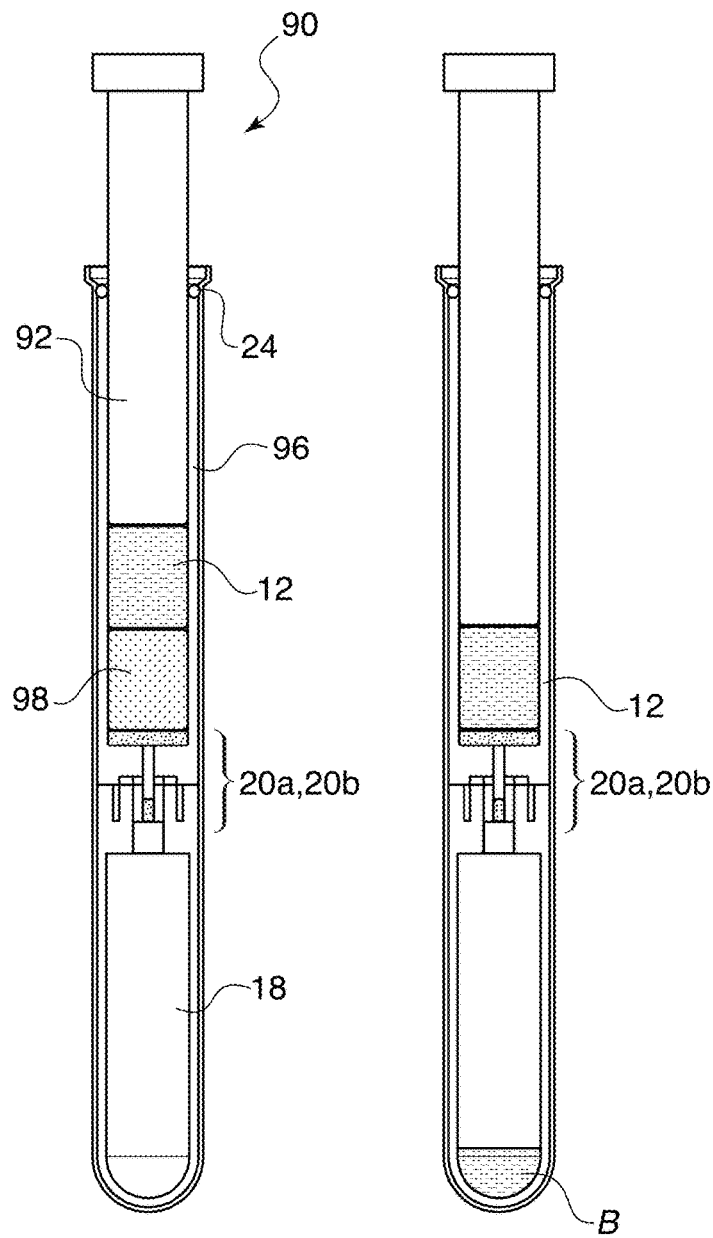
FIGS. 14A-14B show side plan views of a collection container that uses a plunger.

FIG. 14A illustrates an optional buffer/reagent pouch or pad 98 that can be positioned such that buffer/reagent will contact the collected sample during release of the collected sample from the collection pad 12. The syringe may contain a buffer pad or a pouch 98 containing a buffer solution. In one specific example, the buffer pad or pouch 98 may be a porous material that can store any buffer/reagent/additive/liquid additive that can be later extracted through force or fluid flow through the pad or air flow or compression of the pad. It is possible that a buffer/reagent pouch 98 as described here may be included in any of the other disclosed embodiments. Also as described herein, a buffer/reagent pouch 98 may be provided in the device cap 16, or inside the device body 14, in the collection container 18, or anywhere appropriate in the device so that the material of the pouch 98 contacts the collected sample.

In any of the embodiments described herein, the buffer solution may function as a cell and viral particle lysing agent, anti-bacterial, DNA stabilizer, antigen stabilizer, or any combination thereof. The buffer may also contain a chemical that extracts the DNA/RNA from any source (human, animal, bacteria or viruses) which can allow an extraction-free analysis in the lab. Various additional or alternative buffer, reagent, or additional additive options, as well as structures for containing these materials, are described below.

Pressure from the plunger results in squeezing the pad 12 against the buffer/reagent pouch/pad 98 (either directly or indirectly, via way of the filter 20, the cap 16, or any other pressure device). Pouch/pad 98 could also be designed to be punctured in use. Pouch/pad 98 could also be designed to dissolve when comes in contact with saliva or other collected fluid. It should be understood that there are also other methods of breaking the barrier of the pouch/pad 98 that result when the pouch/pad 98 is mechanically squeezed in use. Buffer/reagent is then released and mixed with the collected sample and passed into the collection container 18 connected at the end of the device. If provided as a buffer pad 98, the buffer pad can be made of fibers, foams or sintered particles with varying pore sizes (1-200 microns). The void volume may range from 20 to 99%. The fiber or sintered particles could be made from polyesters, polyurethanes, polyethylene, polypropylene, PTFE, PVDF and elastomeric materials such as thermoplastic polyurethane, and thermoplastic polyethylene or a combination thereof. The buffer pad may be treated to mechanically and/or chemically filter out particulates, protein molecules, or any other type of other debris, contaminants, or desired molecules from the oral fluid sample, such that an additional filter 20 is not required. The buffer pad may contain absorptive additives such as activated carbon, molecular sieves, polymeric absorptive resins, or any of the other additive described throughout this application. The filtrates may include the 5 mucins in saliva (MUC5B-5700AA, MUC7-357AA, MUC1, MUC4, MUC19), bacterial cells, viral proteins, amylases, albumin, or any other appropriate filtrates, or any combination thereof.

In another example of FIG. 14B, a buffer solution "B" is present inside the collection container 18 connected at the end of the device body 14. This embodiment does not use a buffer pad or pouch 98.

In these plunger embodiments, it is still desirable to be able to maintain the seal of the collection container 18 to the device body 14 in order to maintain the sample integrity within the collection container (e.g., not introduce outside air), but still be able to vent air through the collection device.

Accordingly, any of the above described vent options are possible for incorporation with this embodiment as well.

Both FIGS. 14A and 14B show embodiments with alternate filter options, illustrated by FIGS. 15A and 15B. Either filter may be used in either embodiment, or a combination of multiple filters may be used. This differing figures show potential optional locations for the filters. They may be positioned in order to increase surface area for less flow resistance, or to ease manufacturing processes. FIGS. 15A and 15B show option filter 20a, 20b locations. Instead of pressing a dropper to squeeze saliva into/onto a testing device (such as a lateral flow cartridge), the two devices may be connected to each other to natively pass the liquid from the collection device into the lateral flow cartridge. This can make it easier for the user, and less prone to error. Filters 20, 20a, 20b may be made of fibers, foams or sintered particles with varying pore sizes (1-200 microns). The void volume may range from 20 to 95%. The fiber or sintered particles could be made from polyesters, polyurethanes, polyethylene, polypropylene, PTFE, PVDF and elastomeric materials such as thermoplastic polyurethane, and thermoplastic polyethylene or a combination thereof. The filters may be treated to filter out mechanically and chemically filter out large particulates and protein molecules from the oral fluid sample. The filters may contain absorptive additives such as activated carbon, molecular sieves, polymeric absorptive resins. The filtrates may include including the 5 mucins in saliva (MUC5B-5700AA, MUC7-357AA, MUC1, MUC4, MUC19), bacterial cells, viral proteins, amylases, albumin, or any other appropriate filtrates, or any combination thereof.

As described above, the collection container 18 at the end of the device body 14 may be detachable and can be used to ship the sample to a lab for analysis.

In another embodiment of FIG. 16, the device is provided with a mixing chamber 100 instead of a detachable collection container. In this example, the sample collection pad 12 is pressed against a buffer pad/pouch 98, causing the collected sample to flow through one or both of the filter options described, and then into the mixing chamber 100. This mixing chamber 100 could be connected to a lateral flow or vertical flow assay 102 for rapid testing.

In another embodiment, the device may have a collection pad that is permanently attached to the device. The collection pad is exposed during sample collection and retracted once sufficient sample is collected. All other components are within the device along with the collection pad. This provides a one component system. Examples are illustrated by FIG. 17 and FIGS. 32-35. Instead of a separate cap that pushes down on the collection pad to release the collected fluid or instead of a plunger that presses the pad, it is possible for the collection pad to be exposed for collection and then retracted into a body 176 to perform the extraction and/or filtration and/or mixing with reagents inside the device body 176, so that the user does not have to handle multiple parts. This can be similar to retraction of a ballpoint pen into a pen housing.

Referring now to FIGS. 32A-32D, one example provides a body housing 176 that is configured to contain the collection pad 12 therein. The body housing 176 is provided with a swab cap 178 that closes the body housing 176 at one end. Positioned within the body housing 176 is the collection pad 12 and a plunger 180. The plunger 180 has a plunger face 182 that is secured to one end of the collection pad 12. The opposite end of the plunger 180 has a plunger cap 184 that closes the other end of the body housing 176. Associated with the body housing 176 is a collection container 18. As shown in the figures, in this embodiment, the collection container 18 is fluidly connected with the body housing 176 via an optional one-way valve 186. Specifically, the collection container 18 is mounted below the body housing 176. An optional filter 20 is also shown in the fluid path between the body housing 176 and the collection container 18. It should be understood that it is also possible to allow the collected sample to travel directly between the body housing 176 into the collection container 18, without presence of a one-way valve 186 and/or a filter 20. For example, there may be provided in an opening between the two components.

Figure 32A:
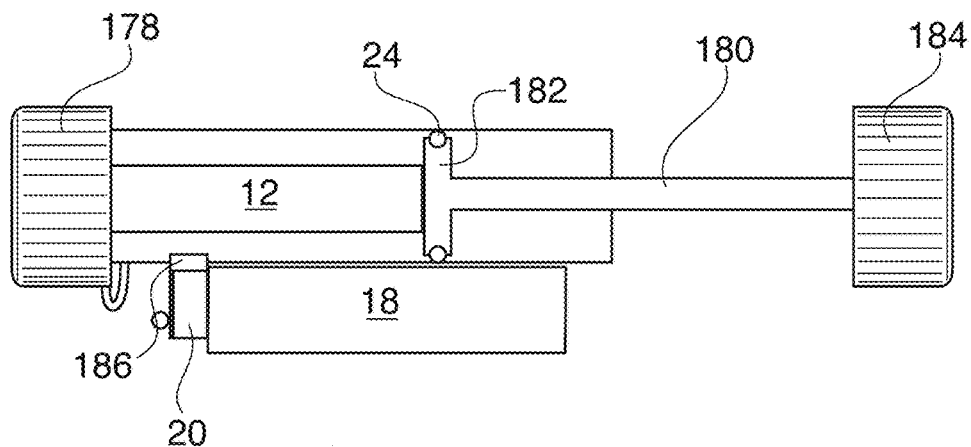
FIGS. 32A-32D show side schematic views of an alternate fluid collection device that incorporates the components into a single device with a push-pop design.

The fluid collection device is provided in the configuration shown in FIG. 32A. The collection pad 12 is covered and maintained in a closed condition via the swab cap 178. The plunger 180 extends away from the body housing 176. The collection pad 12 is covered and maintained in a sterile condition via the plunger face 182 which is sealed by O-rings 24.

Figure 32B:
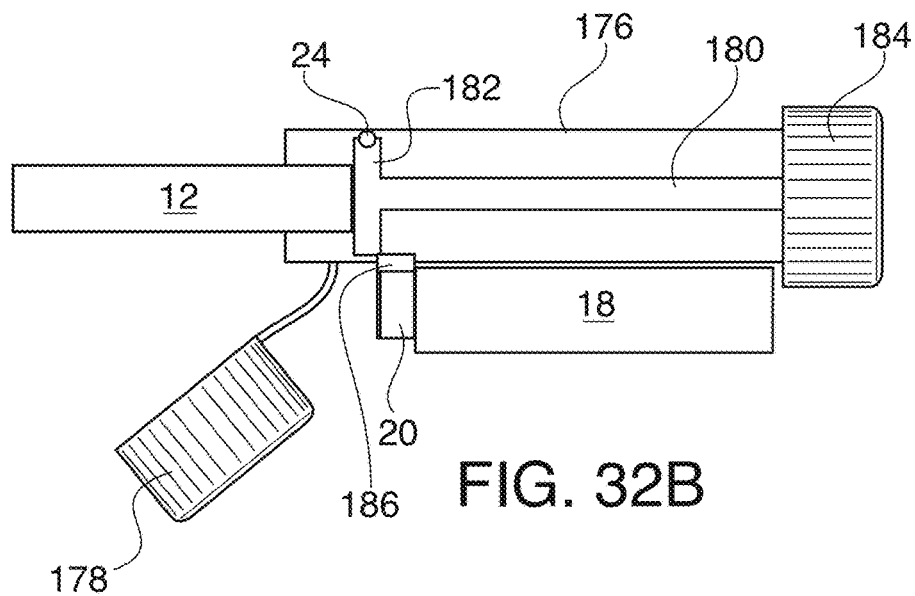

In use, the user opens the swab cap 178 and presses the plunger 180 into the body housing 176 in order to expose the collection pad 12. In some embodiments, the swab cap 178 may be provided with a series of openings and non-openings that are used to allow the collection pad 12 to pass through or push against. In this embodiment, the swab cap 176 always stays "on" the body housing and just rotates through the open and closed positions, much like a dial (similar to a rotary phone). In order to maintain the device as a single piece, the swab cap 178 may be attached to the body housing 176 via a living hinge 188. Once the collection pad has been extended and exposed as shown by FIG. 32B, fluid collection can take place. If the device is used as a saliva collection device, the user can put the collection pad 12 into his/her mouth and soak with saliva. It is also possible to dip the collection pad 12 into the fluid to be collected/tested.

Figure 32C:
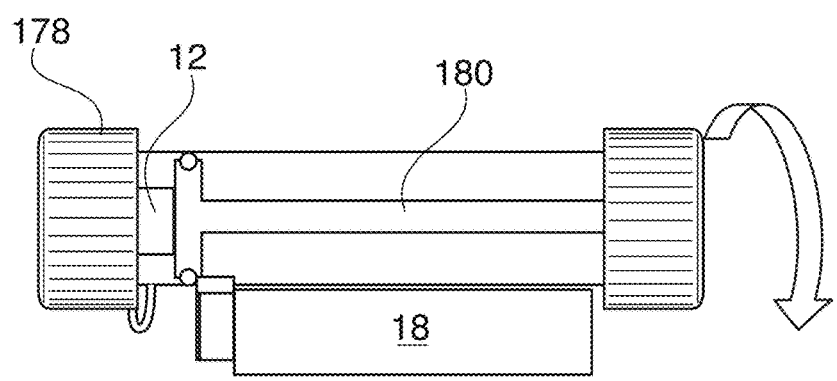
Figure 32:
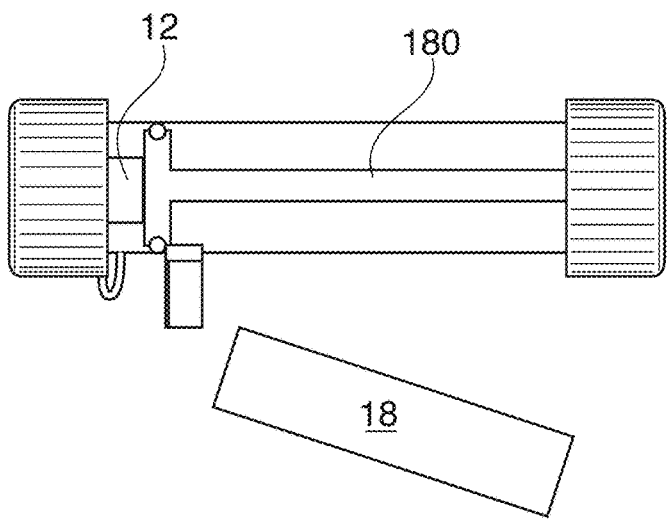

Once collection has taken place, the user retracts the plunger 180 in order to pull the collection pad 12 back into the body housing 176 and replaces the swab cap 178. The liquid collection device will then resemble FIG. 32A. Next, the collection pad 12 is compressed in order to release the fluid collected from the collection pad 12. As shown by FIG. 32C, the plunger 180 is pressed into the body housing 176 in order to compress the collection pad. Collected fluid will be pushed toward the end of the body housing 176, near the swab cap 178. If further compression is needed, it is possible to twist the plunger cap 184 to increase compression. Additionally or alternatively, it is possible to provide a pen click feature to assist with extension and retraction of collection pad 12, as well as compression of the collection pad 12.

As the collection pad 12 is compressed, collected fluid exits the body housing 176 through the one-way valve 186. If a filter 20 is provided, the fluid also passes through the filter 20 on its way to the collection container 18.

Figure 33:
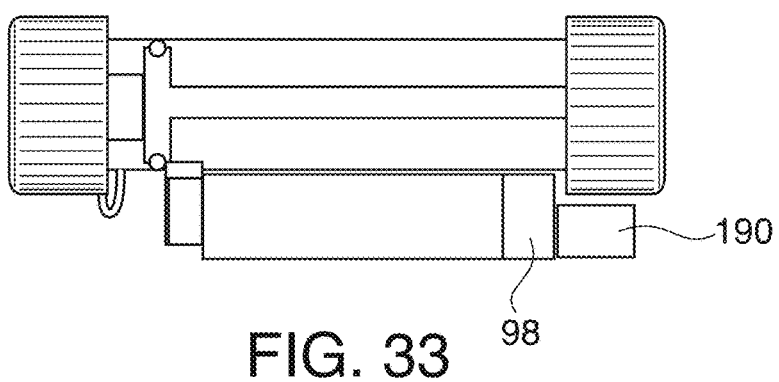
FIG. 33 shows a side schematic view of a fluid collection device that incorporates buffer into the collection container.
Figure 34:
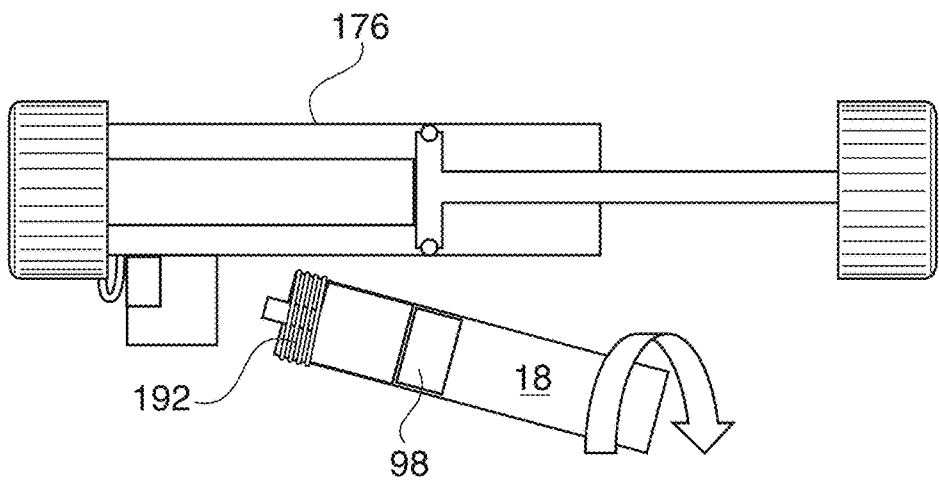
FIG. 34 shows a side schematic view of an alternate collection container attachment.
Figure 35:
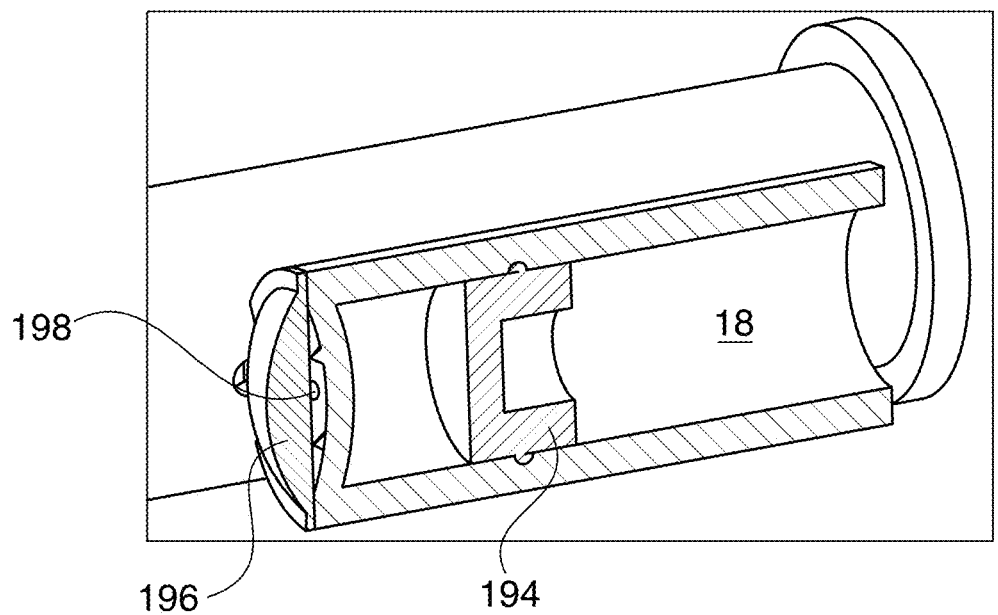
FIG. 35 shows a side cross-sectional view of a collection container of FIG. 34.

Once the fluid has been collected in the collection container 18, it is possible to remove the collection container 18 for further analysis of the collected sample. The collection container 18 may be snap fit to the body housing 176 for easy removal thereof. In one example, the body housing 176 may be formed with an internal groove that receives the external curvature of the collection container 18, as shown by FIG. 35. In another example, the connection between the body housing 176 and collection container 18 is via a threaded or Luer lock connection 192, as shown by FIG. 34. Upon removal, the collection container 18 may be sent to a laboratory or other location for testing. The collection container may have a foil seal at one or both ends to maintain sterility of the collected sample. They collection container may have a needless connection port at one or both ends to maintain sterility of the collected sample. Collected fluid may be extraction via an automated process, as described below. The collection container could also be a permanent/integral part of the device and this port may be used for extraction of fluid using automated liquid handling equipment In one example, the collection container 18 may have a septum to assist with lab analysis. In another example, there may be provided a buffer pouch 98 associated with the collection container 18, as shown by FIGS. 33 and 34. The buffer or other reagent may be released via a separate button that functions as a buffer release 190. This may puncture an internal foil seal, may slide an internal wall to allow mixing with the sample, may be punctured when the plunger cap 184 reaches end of its travel, or may function in any other appropriate manner.

FIG. 34 illustrates an embodiment in which the collection container 18 is secured to the body housing 176 via a threaded or Luer lock connection 192. Check valves may be provided in order to prevent backflow of the collected fluid or leaking when the collection container 18 is removed. As shown by FIG. 35, the collection container 18 may have a movable stopper 194 with a pierce-able septum positioned therein. A blister pack 96 with a piercable-septum can be filled with reagents/buffers/additives and pressed to transfer these solutions via one or more openings 198 into the collection container 18. The movable plunger 194 can provide a replacement for venting, similar to the above-described concepts.

Alternatively, the body may be twisted so that the pad retracts 12 into the body 176. This embodiment may incorporate additional buttons, knobs, handles to push/pull/twist, but not extra components to handle.

Figure 17:
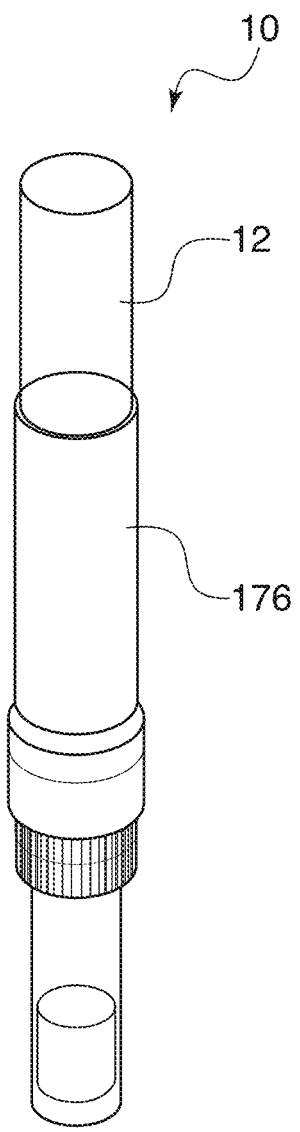
FIG. 17 shows a side perspective view of a fluid container that provides a one-piece device.

FIG. 17 illustrates another example of a one component system. The collection pad 12 can be extended from the body housing 176 via any appropriate manner, such as pen click, twisting, side knobs that extend the pad, or any other method that will allow movement of the collection pad into and out of the body housing 176. Any type of cap described herein may be used to cover the top of the collection pad 12 before and after use.

Figure 18:
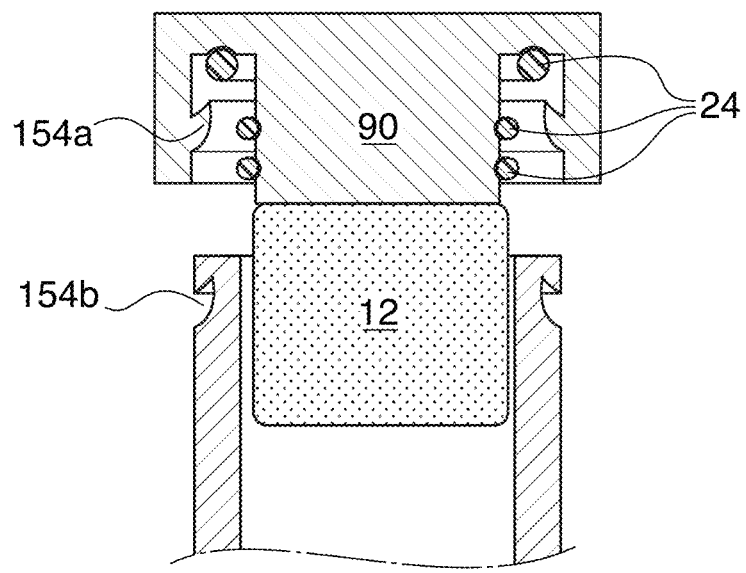
FIG. 18 shows a side cross-sectional view of one locking option.

FIG. 18 illustrates one embodiment of connection 104 between a collection pad 12 and a device body. In this case, the collection 12 pad is connected to a plunger 90 (with o-rings 24) and one end of the ratchet. The plunger head has a series of ratchet lock receivers 154*a*. The device body has a ratchet lock tooth 154*b* at its upper portion. The pad/plunger travels down and compresses the pad inside the device body. The ratchet lock components 154*a*, 154*b* serve to prevent the pad 12 and plunger 90 from being pulled out and used again, or from accidentally exposing anyone to the collected fluid.

Figure 19:
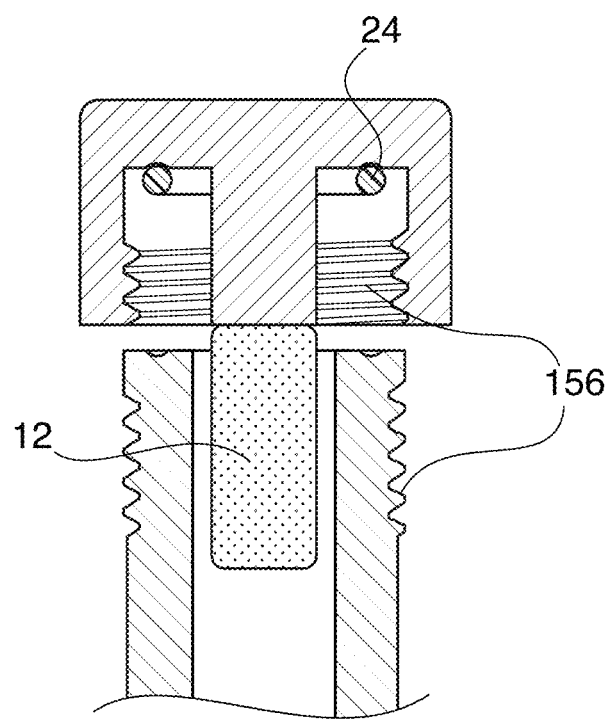
FIG. 19 shows a side cross-sectional view of an alternate locking option.

FIG. 19 illustrates an alternate embodiment of connection between a collection pad 12 and a device body. This embodiment incorporates a threaded lock 156. It is possible for any of the described locking features to be used collectively or individually. It should also be understood that any other type of appropriate locking mechanism may be used. Non-limiting examples include a quarter turn, snap feature, a bayonet lock, a J-hook lock, or any combination thereof.

Reagent/Additional Additive/Buffer

A reagent material or additional additive or buffer may be incorporated into the liquid collection device 10. The design of the disclosed device can allow for automatic mixing of the reagent/additional additive/buffer with the collected sample without any additional steps required by the user. The material can be provided pre-loaded with the device. Non-limiting exemplary options of how the material may be incorporated are provided.

This material may be on or within the filter 20, the collection pad 12, the cap 16, the collection container 18, in a mixing chamber, in a separate pouch, or provided as an additional component or as any part of the device in the fluid path between collection pad and the collection tube. In general, a reagent or additional additive may be provided or otherwise incorporated into one or more components of the liquid collection device in any way that allows or otherwise causes the reagent or additional additive to contact the collected liquid sample.

In a specific example, the buffer or other reagent or additive material may be a liquid contained in the cap 16 (within an absorbent pad or by itself) such that, when compressed with the collection pad 12, the material is released and flushes the collected sample through the collection pad 12 and into the collection container 18. (If an optional filter is provided, the sample may also pass through the filter during compression.) If a filter 20 is provided, the filter 20 may contain the same liquids or a powder versions of the material that can be reconstituted when saliva comes in contact with the material. In another example, the material may be provided in its own mixing chamber. Exemplary buffer or other reagent or additive materials are described further below.

The reagent or additional additive could be loose material, a liquid in a pouch, in a swab, in a membrane, in a foil seal that is pierced or broken for release, in a powder form that is reconstituted when the liquid sample passes by or through it, in a form of a pellet (formulated pill), as a capsule provided in the collection container or any part of the device, or any combination thereof.

In one example, a reagent or additional additive may be provided in the collection pad. In another example, the filter may be treated or at least partially coated with a reagent or additional additive. In another example, a reagent or additive may be stored behind a barrier that dissolves when it comes in contact with liquid. In another example, a reagent or additional additive may be stored in a cap, such that the reagent or additional additive is released when the cap applies pressure to the collection pad. For example, a reagent or additional additive may be provided in a swab positioned within the cap that can be dosed with the reagent/additional additive and released upon compression in order to mix with the collected sample. A reagent or additional additive may be provided in a foil seal that is broken/released upon pressure. In another example, a reagent or additional additive may be liquid, powder, a coating on an interior of any part of the collection container (e.g., its walls or base), or a loose liquid contained in the collection container, or any other appropriate component that can contact the liquid sample while it is contained within the liquid collection device. Any combination of the above options may be incorporated with one another.

Non-limiting examples of reagents/additional additives include but are not limited to a buffer (dried or in solution), a preservative, a cell or a viral particle lysing agent, a viral inactivation agent, a chemical inactivator that can inactivate infectious particles but leave them intact for later testing, a bacterial static solution that does not kill bacteria but prevents further bacteria growth, a particle stabilizer (e.g., a DNA stabilizer or antigen stabilizer), an antibacterial, cortisol, progesterone, a viral transport media (VTM), dye, organic solvent (to precipitate/isolate the DNA/RNA), reagent required by assay, beads for grinding, beads with antibody/antibodies, flavorings, stimulants to induce saliva production, chemicals that can create an isothermal reaction to raise or lower the temperature of the solution (for controlling bacterial or viral growth, inactivation, transportation stabilization, or even to induce molecular diagnostic reactions such as LAMP—Loop-mediated isothermal amplification), a reagent or additive that can react with collected sample and provide a diagnostic result shown as color changed liquid in the final collection container or collection window, or any combination thereof.

More specifically, the reagent or additional additive may be an inactivation buffer. One example is a lysis buffer. Exemplary compositions of possible buffers are outlined in the below table:

| | |
|---|---|
| Option 1 | alcohol (<24%), Sodium dodecyl sulphate 1-5% Glycine, N,N'-trans-1,2-cyclohexanediylbis[N-(carboxymethyl)-, hydrate 1-5% Lithium chloride 0.5-1.5% |
| Option 2 | Ethanol 10-25% Tris 1-5% Thiocyanic Acid: Guanidine (1:1) 25-50% pH 7.9-8.3 |
| Option 3 | Recipe 3: Ethanol <24% Tris 1-5% (host DNA stabilization) |
| Option 4 | 0.3% TnBP (tri-n-Butyl phosphate) |
| Option 5 | 150 mM NaCl, 1.0% IGEPAL ® CA-630, 0.5% sodium deoxycholate, 0.1% SDS, 50 mM Tris, pH 8.0. |
| Option 6 | 2% FBS, 100 µg /mL Gentamicin, 0.5 µg /mL Amphotericin B in Hanks Balanced Salt Solution |

Possible buffers will typically include one or more of the following components, either alone or in various combinations: tri-n-Butyl phosphate; Tween® 80 (Polysorbate); Triton® X-100; Sodium laureth sulphate; Benzalkonium chloride; Chlorhexidine; Chlorhexidine with CphC; CPyC; Ag nanoparticles suspension; Polymers; polyethylenimine (PEI) disrupt lipid envelope; β-cyclodextrins (βCDs); Proteinases; protease K; Brij-97; LDAO; QACs; LAS; or any combination thereof.

One general goal of the reagent or additional additive is to allow release of analytes from the collection pad for later testing. Another general goal of the reagent or additive is to preserve the sample for later analysis, or to enhance the overall safety or efficacy of the collection system.

Additional Features.

The device can be designed to ensure ease of transfer for high throughput lab processing using automated equipment. For example, the collection container could have a cap that allows for direct connection to automation equipment to remove samples in the lab or at the point of care. The device could have a sample extraction port so the user sends the whole device to the lab (once sample collection is complete) and the lab can just drop the device into the automation equipment. The device can have QR codes with sample information and can allow results be scanned into a database through an app to issue a certificate of testing.

Automation/Testing

FIGS. 36-39 illustrate how a fluid collection device 200 may be used directly in an automated liquid handling machine. This disclosure is generally focused on use of the entire device (e.g., with an integral collection container), but it should be understood that a removable collection container 18 may similarly be used and tested as described. Automated liquid handling machines typically have a plurality of racks 210 that hold samples to be tested. Typically, the automated device has a plurality of pipettes with pipette tips 204 that are inserted into the sample to be tested. The pipette tips 204 may also be provided with a pipette tip filter 202, which may have any of the disclosed features of the filters described herein. (The pipettes are usually attached to a robotic arm that lifts and lowers pipettes and moves them from sample to sample, such automated liquid handling machines are generally well understood in the art.)

Figure 36:
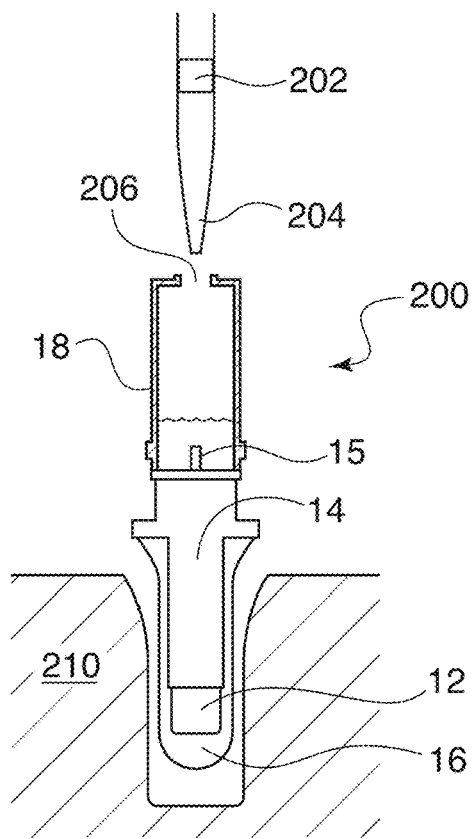
FIG. 36 shows a schematic view of a fluid collection device configured to be used in connection with an automated liquid processing machine.
Figure 37:
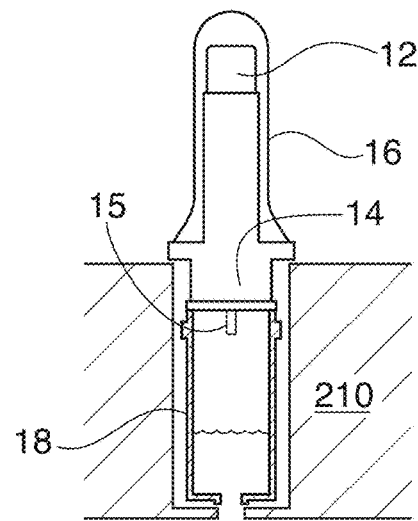
FIG. 37 shows a schematic view of the fluid collection device of FIG. 36 in a collection rack designed to receive the device inverted.

It is possible to design a custom rack 210 that is designed to fit one or more embodiments of the disclosed fluid collection device 10, 200, its tubular body 60, 112, 176, or any other component. The device can be designed to allow the liquid handling robot to directly pull the collected sample out of the device without having to remove the cap 16. A user can insert the device into the rack 210, and the liquid handling machine can remove the collected sample through an access point of the collection container. In a specific example, the access point is a port 206 in the collection container 18. The port 206 can be designed to receive a pipette top 204. (This port 206 could be a needleless port, could incorporate a port valve, could be an access point covered by a foil (or other accessible) seal, or any other appropriate access point/port option.) The nozzle 15 and gasket (shown immediately below the nozzle 15 in FIG. 36) can function to create a pool of the collected sample. As shown by FIG. 36, the collected sample could be collected out of the device via the bottom of the device. As shown by FIG. 37, it is also possible to insert the device into the rack 210 upside down and access the collected sample from underneath the device, through a port 206 at the bottom of the device.

Figure 38:
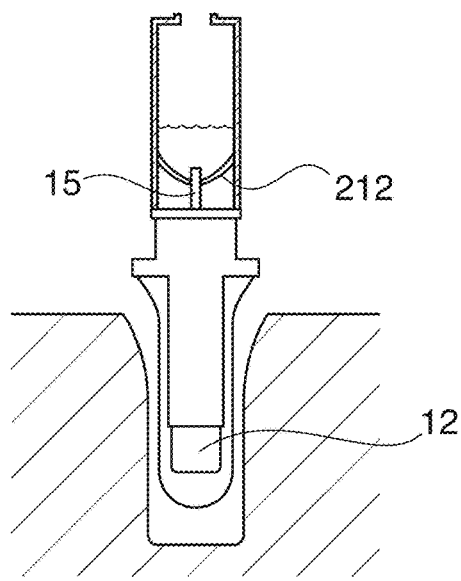
FIG. 38 shows the fluid collection device of FIG. 36 with a collection feature.
Figure 39:
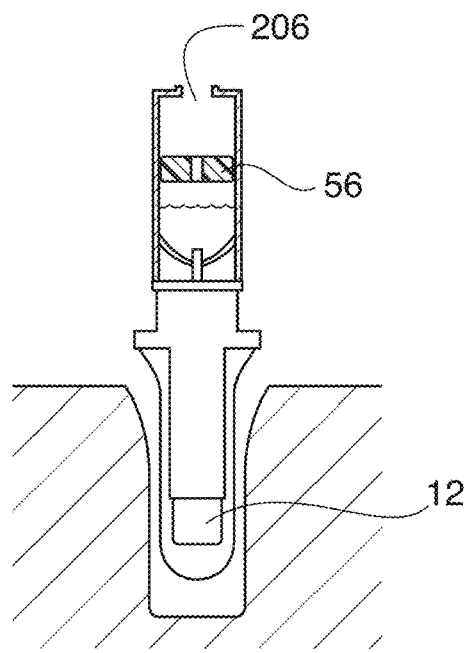
FIG. 39 shows the fluid collection device of FIG. 38 with a movable base.

FIG. 38 illustrates one embodiment that incorporates a collection feature 212 that cooperates with the nozzle 15. The collection feature 212 can function similar to a funnel, and it can receive the nozzle 15 for pooling the collected sample. It is also possible to provide a one-way valve that will prevent reverse liquid flow of the collected sample back into the device body. FIG. 39 illustrates an embodiment with a movable plunger 56. The movable plunger 56 may have a central port extending therethrough that can receive the pipette tip 204 for retrieving the collected sample.

Data Collection

The device may be provided with a unique bar-code identifier on a label placed on each device or on the collection container that is later disconnected and sent to the lab for further processing. This unique identifier can be used to help trace the device and link test results in a system to an individual. This linking may be done via a mobile app. The device may include a QR code that can automatically download and install an app prior to testing. The app can automatically include information on the unique identifier.

The developing company can generate and maintain a database of test results. It is also possible to integrate the identifier with apps and databases created by other assay developers. During testing, the unique identifier can be automatically scanned into the system using the bar code. Test results that are generated can be automatically linked to this identifier. The app can then connect to the database of test results, and read and display the results along with a time stamp. This can allow test results to be displayed to the end user. In some public disease situations or outbreaks, the database/app can also generate a "passport" to allow easy access to public venues. In a specific example, if the test of the sample is conducted to determine whether a tested subject has COVID or some other virus or affliction, the testing can be relayed to the patient to allow the patient to show that s/he is "cleared/free of virus antibodies" in order to board a flight, gain access to a public gathering, show family members and friends that they are clear, or any other purpose.

Incorporated Test Strip.

The next set of figures provides embodiments that incorporate devices that function to collect an oral fluid sample from a patient, mix that sample with a buffer, and then contact the mixed sample/buffer with a test strip. Various options for the device are described herein. It should be understood that these are provided as examples only and that any of these plunger/test strip embodiments may be modified for use in connection with the above described device 10 of FIGS. 1-5. A number of these examples incorporate use of a system that uses a buffer container 110, a syringe 112, a swab plunger 114 with an attached collection pad 12, and a test strip 116 supported therein.

Figure 20A:
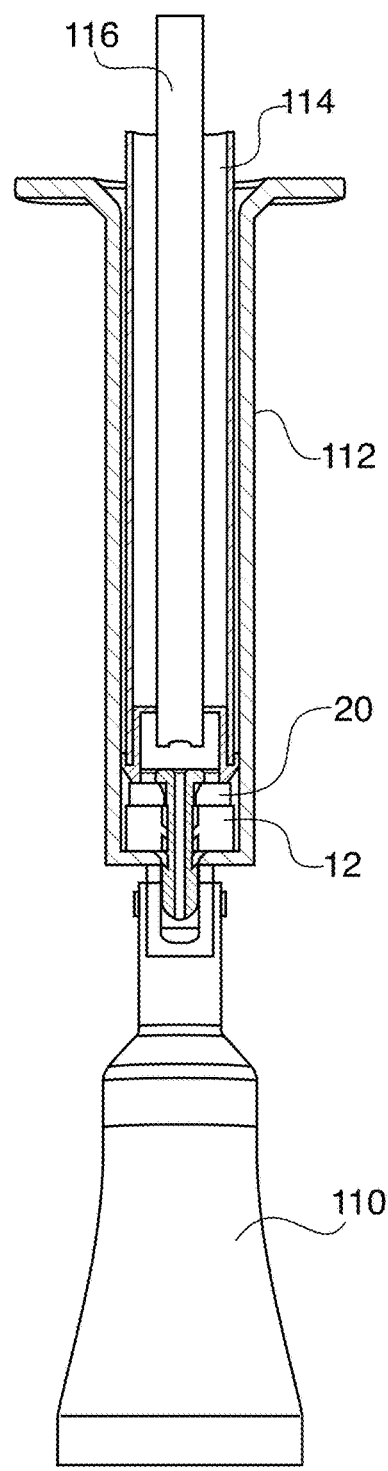
FIG. 20A shows a side cross-sectional view of fluid collection device that incorporates a separate buffer container and a test strip.
Figure 20B:
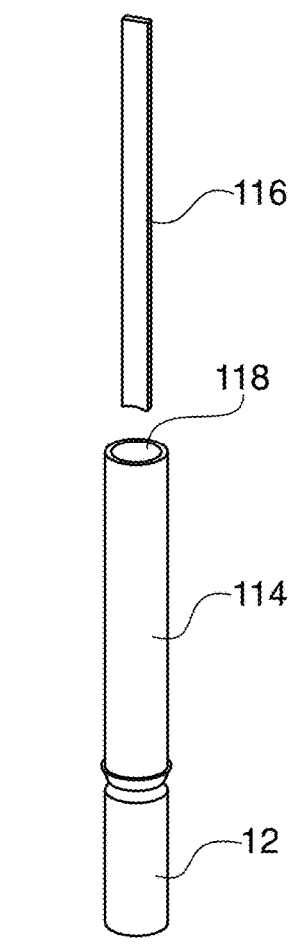
FIG. 20B shows a side perspective view of a swab plunger and test strip.
Figure 20C:
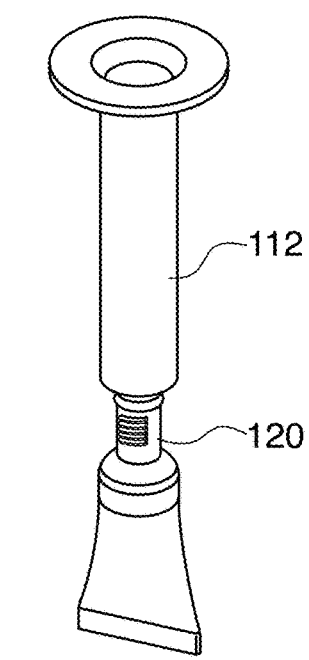
FIG. 20C shows a side perspective view of a buffer container and a tubular body.

In the embodiment illustrated by FIGS. 20A-20C, a test strip 116 is positioned within an internal channel 118 of a swab plunger 114. A buffer container 110 may be a buffer ampule that is secured to an end of the syringe 112 via an adapter 120 or any other appropriate connection mechanism. (As mentioned above, the syringe may be the device body 14 or any other tubular structure that provides support for the functions of the disclosed system.) A sample is collected on the collection pad 12 of the swab plunger 114. After the sample is collected, the swab plunger 114 is inserted into the syringe 112. A plunger is compressed, driving the collected fluid through a filter 20 positioned within the syringe 112. The buffer ampule package is unsealed and squeezed into the syringe 112 to send buffer through the collection pad 12 and filter 20. When the collection pad 12 is compressed against the base of the syringe 112, the collected liquid is forced up through the filter 20 into the body swab plunger 114 positioned within the syringe 112. The syringe 112 thus functions as a collection container as well. This embodiment can help ease manufacturing because the buffer ampule 110 is a separate component such that buffer is not required to be contained within the plunger (or other type of device body) itself.

Figure 21:
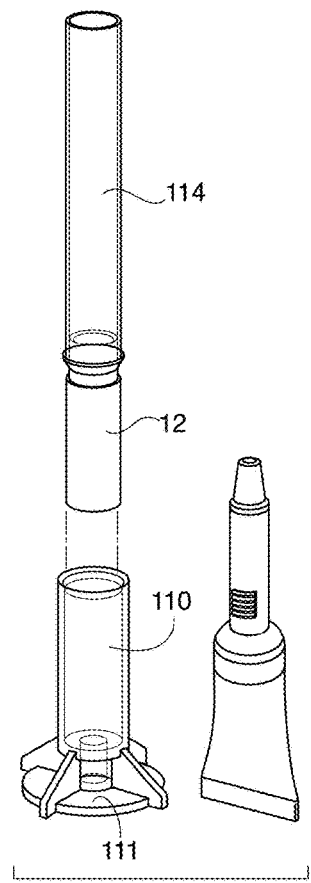
FIG. 21 shows an exploded view of a buffer cup and a plunger swab.
Figure 22A:
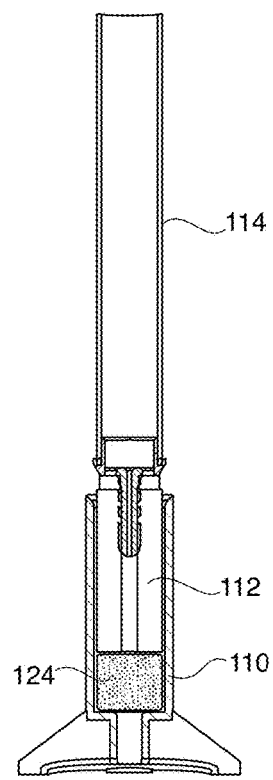
FIGS. 22A-22B show side cross-sectional views of a plunger swab in position in a buffer container, using a buffer sponge.
Figure 22B:
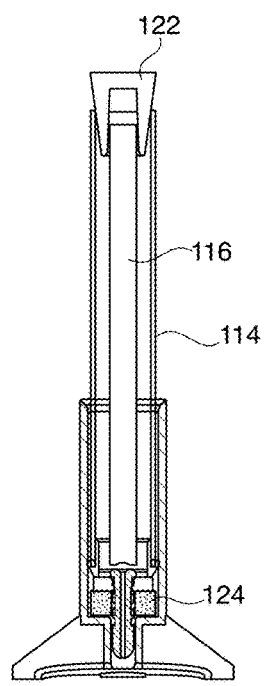

FIGS. 21 and 22A-22B illustrate a buffer container 110 that is a buffer cup with a flat base 111 that can be used on a flat surface. In this embodiment, buffer can be poured into the buffer cup 110, and the collection pad 12 can be pushed via a plunger/swab plunger 114 into the buffer container 110. A diagnostic test strip 116 can then be positioned within the swab plunger 114 to contact the collected sample. This embodiment (as well as any others disclosed herein) also may include an optional cap 122, which can help prevent the exposure and leakage of sample into the test area. This embodiment alleviates the need for a syringe 112. The flow of collected fluid, once the collection pad 12 is compressed, is back up through the collection pad 12 and into the swab plunger 114.

FIGS. 22A-22B provide a similar embodiment, but incorporates a buffer sponge 124 that can be positioned within the buffer container cup 110 that can be used to contain the buffer, rather than pouring the buffer directly into the buffer cup 110. This option can help prevent spillage or evaporation of the buffer solution.

Figure 23:
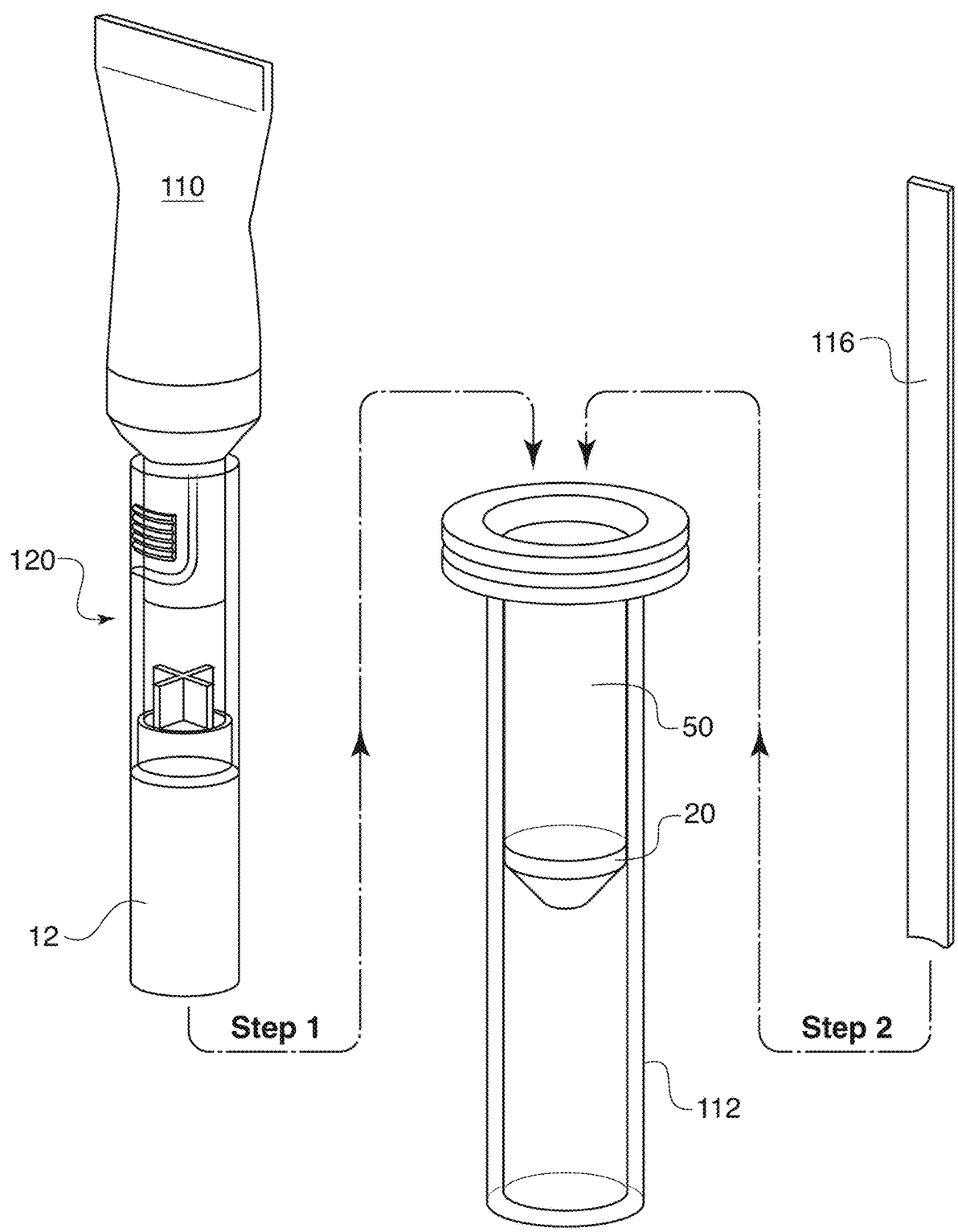
FIG. 23 shows an exploded perspective view of a buffer container that can be connected directly to a collection pad.
Figure 25A:
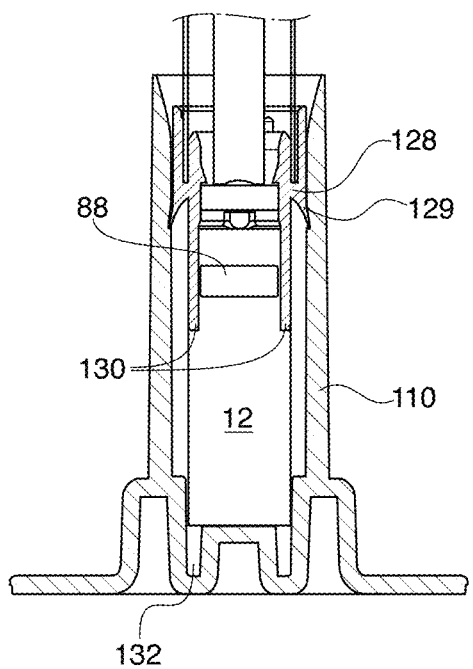
FIGS. 25A-25B show side cross-sectional views of a hard outer seal using an adapter with legs.
Figure 25B:
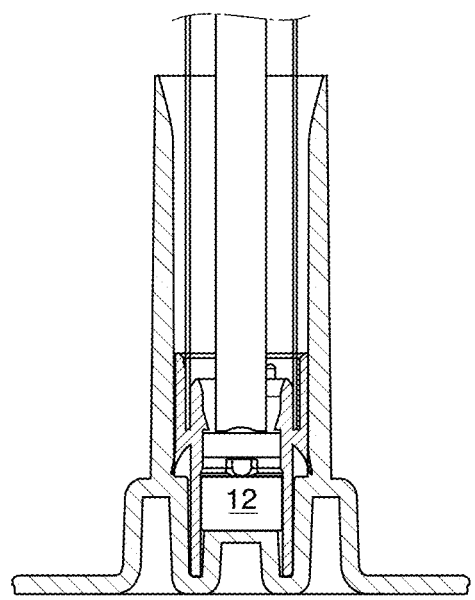

FIG. 23 uses an inverted buffer option. In this version, the buffer container 110 may be connected to the collection pad 12 via an adapter 120. The buffer container 110 is attached directly to the collection pad 12 so that buffer can be pushed through the collected fluid sample, ensuring greater recovery of analyte from the sample. The buffer flushes the sample out of the collection pad, not replying completely on compression only. After sample collection, buffer solution is squeezed through the sample collected on the collection pad 12, and the pad 12 is pushed into the collection tubular body 112. The tubular body may include a filter 20 and/or a funnel 50. It is possible to use the funnel 50 in order to help guide the buffer/sample into the collection container 112. The funnel 50 can act as a stop to allow compression of the collection pad 12 and extraction of the fluid/saliva down through the funnel opening. The collection pad 12 and funnel 50/filter 20 can be removed, and then a test strip 116 inserted into the collection container.

A further embodiment provides a buffer solution inside a glass (or breakable) ampule. One example is illustrated by FIGS. 24A-24B. In this example, the sample is collected as described herein with the collection pad 12. The collection pad is inserted into a buffer container 110 (in this example, it is shown as the embodiment having a flat base 111) and pressed against the bottom of the container 110 in order to displace the collected fluid upward. A main tubular body 112 with a glass buffer ampule 150 contained therein can been positioned over the buffer container 110. The main tubular body 112 can then be squeezed in order to break the buffer ampule 150 inside so that the buffer material mixes with collected fluid sample. As shown, a test strip 116 can also be provided in the tubular body 126. In a specific example, the tubular body 112 is clear/transparent so that mixing and reading of the test strip is easily viewable. This breakable ampule concept is possible for use in alternate embodiments described herein. For example, it may be used in connection with the embodiment of FIGS. 20-23, where, instead of the buffer squeeze tube 110 container attached to the collection pad 12, there can be a housing with a breakable ampule.

Another embodiment elaborates further on the various buffer options described above. In this version, if the buffer container 110 and the tubular body 112 are provided in transparent plastic or other see-through material, it is possible for the plunger itself to act as a sample sufficiency indicator. For example, when the collection pad 12 is moistened, it may become translucent, indicating that it has collected enough fluid. In another embodiment, the collection pad 12 could be designed to change colors when contacted with fluid. In further embodiment, there may be provided a foam component between the plunger and the swab. If the foam becomes moistened, it can change color based on a pH reaction, a thermochromatic reaction, or other aqueous reaction, indicating sufficient sample has been collected/received by device.

FIGS. 25-29 illustrates various ways that the collection pad 12 can be secured to the swab plunger 114 so that it can be inserted into the syringe, vial, tubular body 112, or other collection container. In one example, the collection pad may be friction fit in place. In other examples, there may be provided an adapter 128 that is positioned to secure the collection pad 12 in place. In the example shown by FIG. 25A, an adapter 128 is provided with extended legs 130 that extend at least partially down the collection pad 12. In use, when the collection pad 12 is compressed into the buffer container 110, the extended legs 130 press down into receiving grooves 132 of the buffer container 110. Fluid is released from the collection pad 12 by its being pushed in to the bottom of the container 110, as shown by FIG. 25B. These figures also illustrate a "hard seal" option, where the adapter has side wings 129 that act as the seal between the tubular body 112/plunger instead of using an o-ring. This concept can be incorporated into any of the described embodiments in order to eliminate one or more o-rings in the design. Instead, any of the disclosed embodiments may incorporate a hard seal between the device body and the cap or other feature. FIG. 25A also illustrates an optional sample sufficiency indicator 88, which may also be incorporated into any of the disclosed embodiments.

Figure 26:
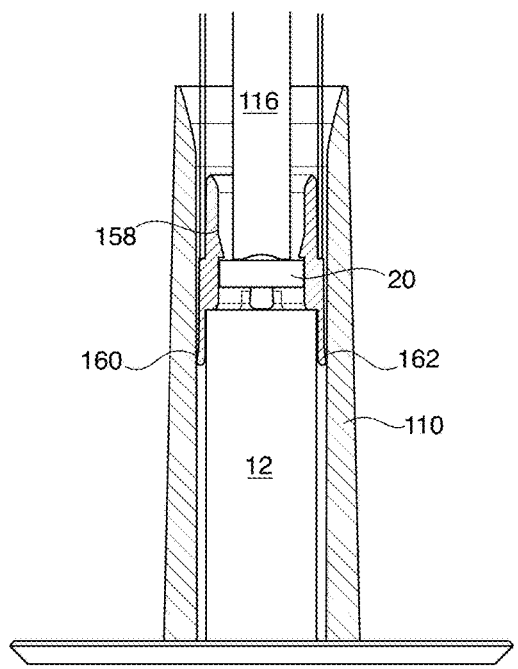
FIG. 26 shows a side cross-sectional view of an adapter using winged legs as a hard seal.
Figure 27:
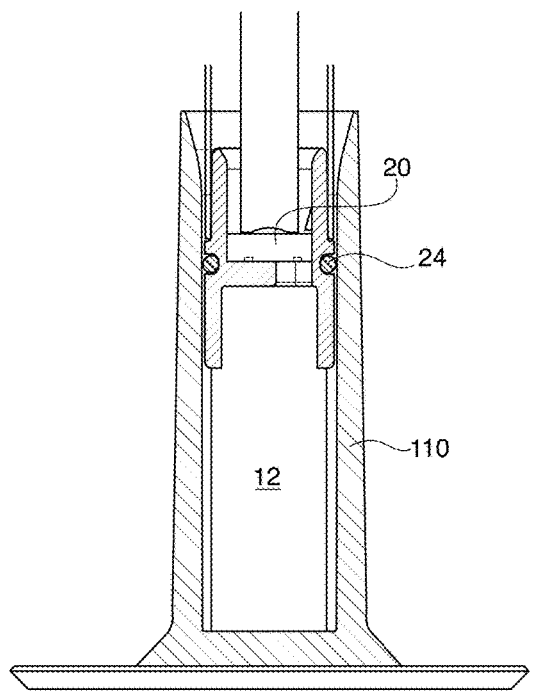
FIG. 27 shows a side cross-sectional view of an embodiment that uses O-rings to create the seal.

In another example shown by FIG. 26, a hard seal may be created inside a tube or buffer cup 110. In this example, there is a hard seal ring 160 with outwardly turned legs 162. This hard seal ring 160 can be injection molded (making the device easier to manufacture) and can replace the o-rings of other versions. Alternatively, o-rings 24 may create the required seal, as shown by FIG. 27.

Figure 28A:
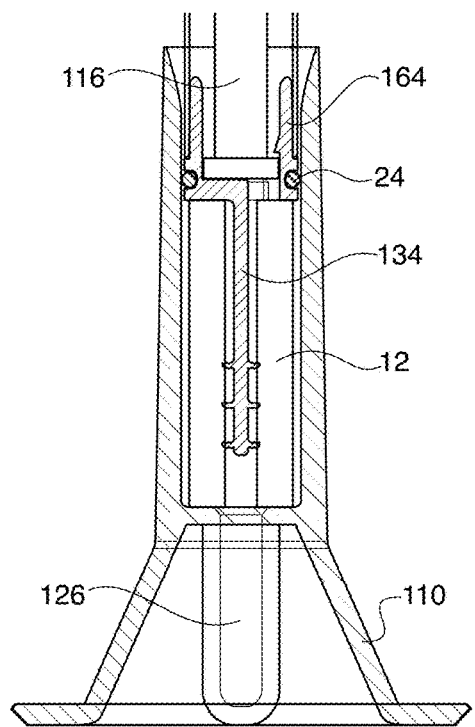
FIGS. 28A-28B show side cross-sectional views of a barb used to secure the collection pad.
Figure 28:
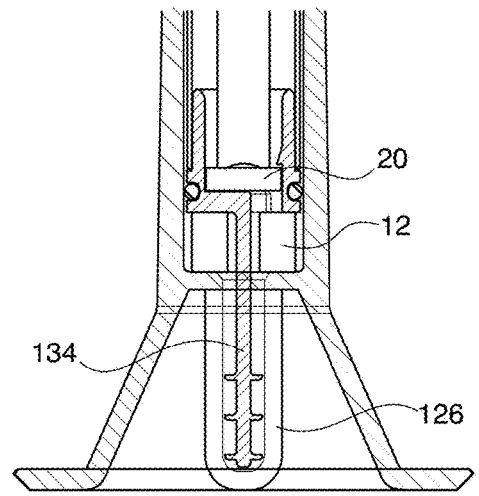

In a further example, the collection pad 12 may be held or otherwise supported by a barb 134 that extends from the plunger. One example is illustrated by FIGS. 28A-28B. In this example, the tube or buffer container 110 may be provided with a recessed well 126 shaped to receive the barb 134 upon compression of the collection pad 12.

Figure 29:
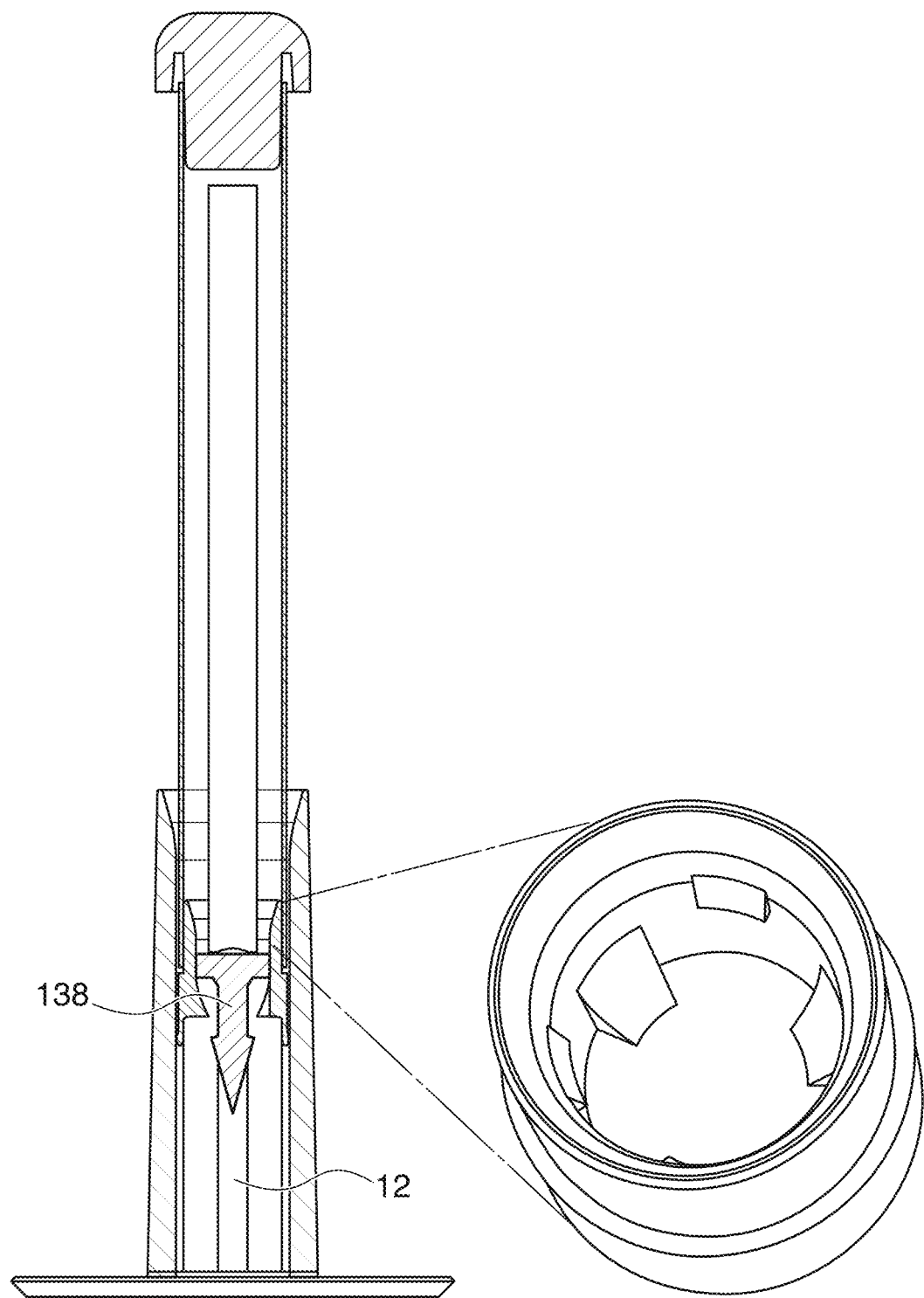
FIG. 29 shows a side cross-sectional view where in the filter is formed as a barb to secure the collection pad.

In a further example, the filter itself is a filter barb 138. Other shapes are possible and considered within the scope of this disclosure. The general concept that the filter itself can create a mechanical lock with the collection pad 12. One example is illustrated by FIG. 29.

Figure 30A:
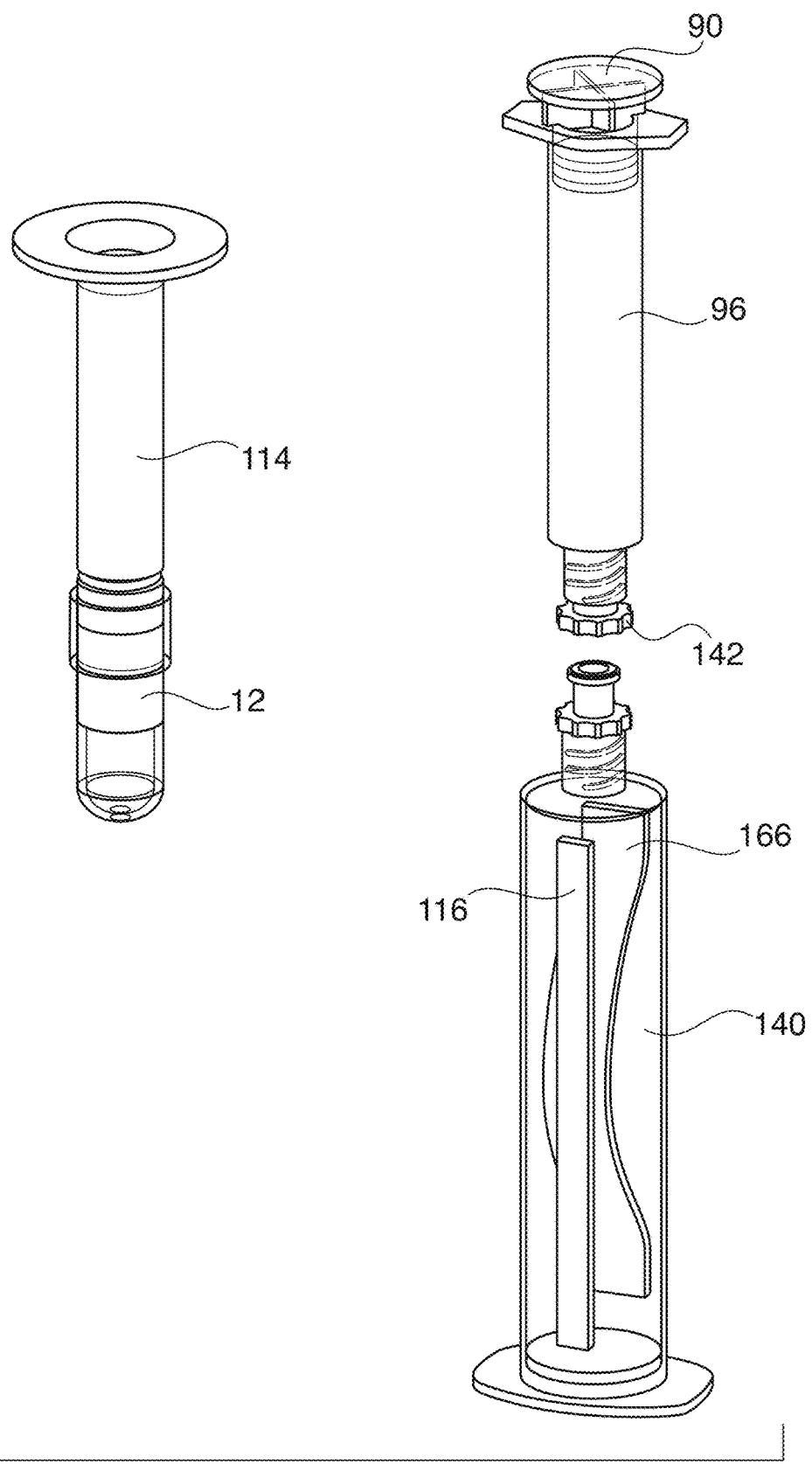
FIGS. 30A-30B illustrate side exploded views of fluid collection devices using off-the-shelf plungers and syringes.
Figure 30B:
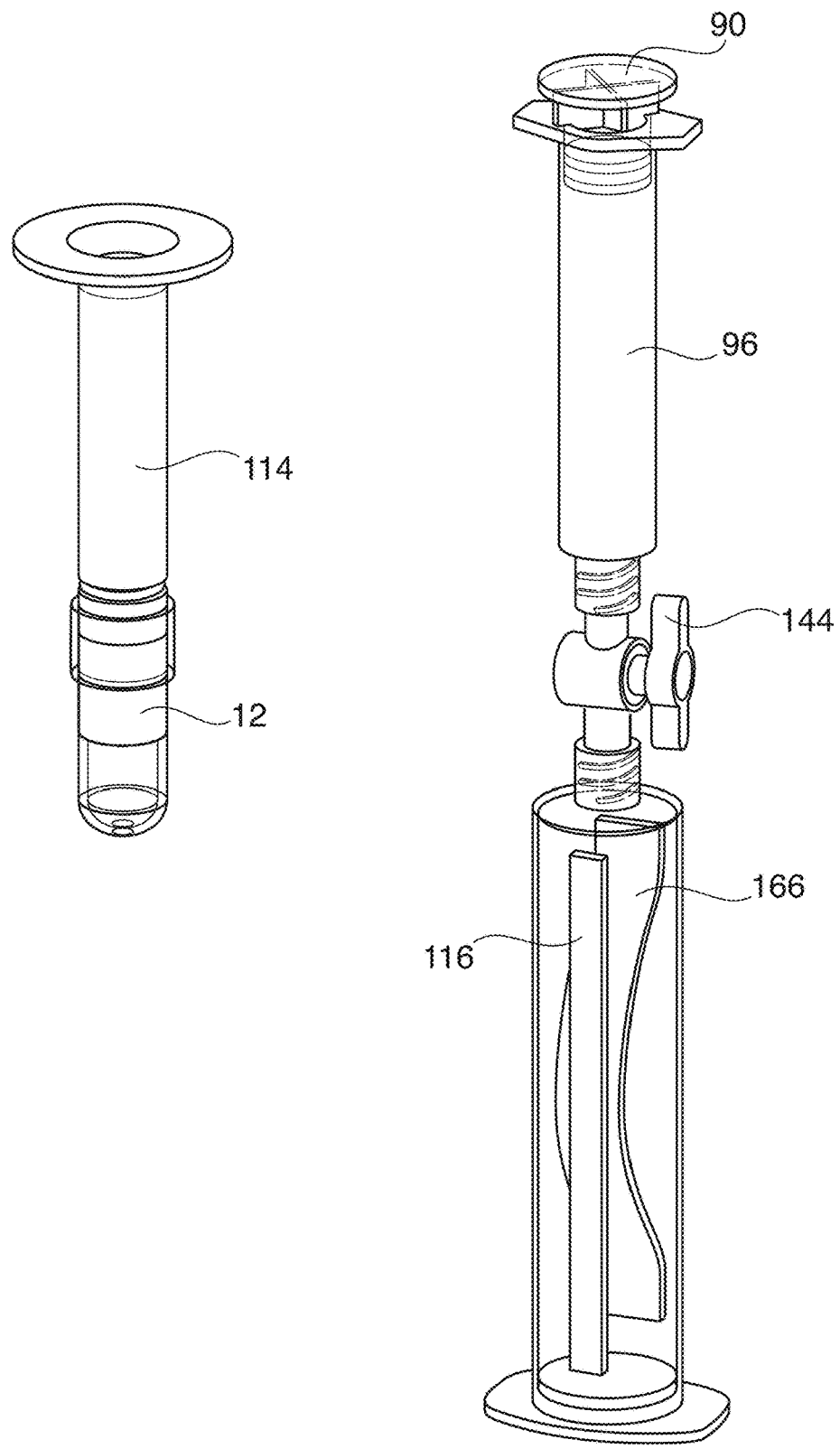
Figure 31:
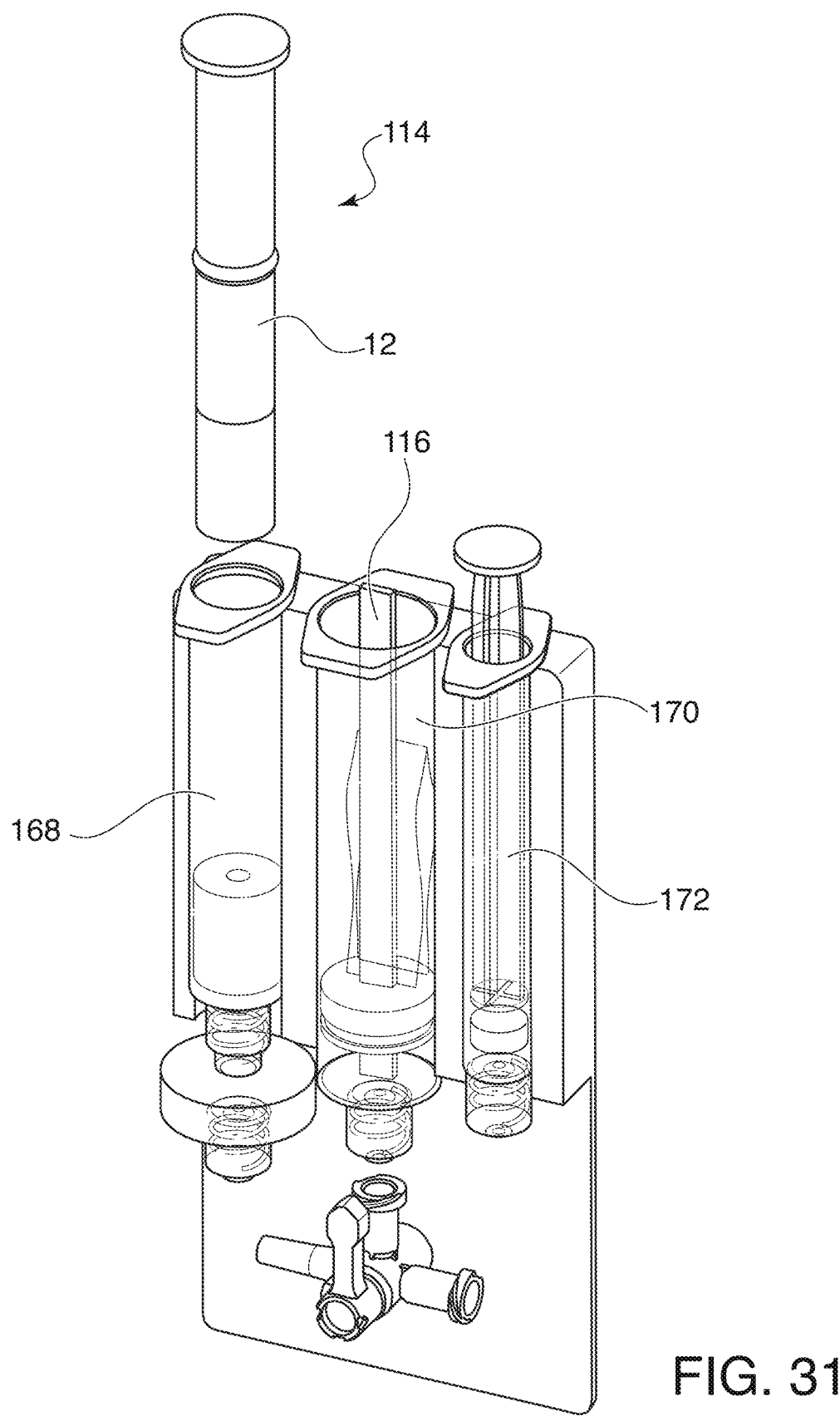
FIG. 31 illustrates a side perspective view of a fluid collection device using off-the-shelf plungers and syringes pieced together into a collection and potentially test cartridge.

A further embodiment shown by FIGS. 30-31 illustrates that the disclosed oral fluid device can be designed with off-the-shelf syringes and other components. In one example, the buffer may be preloaded into or absorbed into a sponge. Fluid may be collected on a collection pad 12, then the swab plunger 114 with the collection pad 12 may be positioned into a syringe body 96 such that liquid is allowed to bubble into a lower test tube 140, which functions as a collection container. One example shown by FIG. 30A uses a luer cap 142 to connect the syringe 96 and the test tube 140. Another example shown by FIG. 30B uses an integrated valve 144 to connect the syringe in the test tube. FIG. 31 illustrates use of off-the-shelf syringes and valves. There is shown a collection syringe 168, a test syringe 170, and a buffer syringe 172.

Any combination of any of the above described features of any components of the disclosed liquid collection device may be interchanged with one another as possible and considered within the scope of this disclosure.

The subject matter of certain embodiments of this disclosure is described with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

It should be understood that different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A fluid collection device, comprising:
   a collection pad;
   a device body; and
   a collection container,
   wherein the collection pad is secured to a first end of the device body and wherein the collection container is removably secured at a second end of the device body, wherein once sample collection has taken place, compression of the collection pad forces sample collected by the collection pad to move through the device body and into the collection container, wherein the collection container is configured to be removable from the device body to allow separation of the collected sample from the collection pad and the device body.

2. The device of claim 1, wherein the collection container is threadingly secured to the device body.

3. The device of claim 1, further comprising a nozzle positioned within the device body for directing collected fluid.

4. The device of claim 1, wherein fluid collected via the collection pad is collected at a first end of the collection pad, travels through the collection pad, and exits at a second end of the collection pad, into the collection container.

5. The device of claim 1, further comprising a filter positioned to filter collected fluid.

6. The device of claim 5, wherein the filter comprises fiber components, track-etched-membranes, sintered particles, or any combination thereof.

7. The device of claim 1, further comprising a cap with a length configured to be positioned over and cover the collection pad.

8. The device of claim 1, further comprising a buffer, additive, or reagent incorporated into the fluid collection device.

9. The device of claim 8, wherein the buffer, additive, or reagent is incorporated into the collection device via any of the following or any combination thereof:
   (a) a cap that is positioned over the collection pad and when pressure is applied to the collection pad via the cap, the buffer additive, or reagent is released;
   (b) a filter through which collected fluid travels on its way to the collection container;
   (c) in the collection container;
   (d) in a buffer pouch that releases buffer during use;
   (e) in a separate buffer container; or
   (f) in a separate buffer sponge.

10. The device of claim 1, further comprising a funnel positioned with respect to the device body.

11. The device of claim 1, wherein the collection container comprises a dropper bottle.

12. The device of claim 1, further comprising one or more venting features.

13. The device of claim 12, wherein the one or more venting features comprises a porous vent gasket, threads between the device body and the collection container, an exhaust vent, a plunger, or a vent tube with side openings on the device body.

14. The device of claim 1, further comprising a sample sufficiency indicator.

15. The device of claim 1, further comprising a moveable base.

16. The device of claim 1, wherein a seal between the device body and the collection pad is created by an adapter.

17. The device of claim 1, further comprising an access point on the collection container configured to allow sample extraction from a collection container that remains integral with the device body or from a collection container that is removed from the device body.

18. The device of claim 1, further comprising a cap for the collection container, such that, once the collection container is removed from the device body, the cap is configured to be placed over an opening of the collection container in order to secure collected sample therein.

* * * * *